(12) United States Patent
Zeikus et al.

(10) Patent No.: US 7,838,282 B2
(45) Date of Patent: Nov. 23, 2010

(54) ELECTRODE COMPOSITIONS AND CONFIGURATIONS FOR ELECTROCHEMICAL BIOREACTOR SYSTEMS

(75) Inventors: Joseph Gregory Zeikus, Okemos, MI (US); Doo Hyun Park, Seoul (KR)

(73) Assignee: Board of Trustees of Michigan State University, East Lansing, MI (US)

( * ) Notice: Subject to any disclaimer, the term of this patent is extended or adjusted under 35 U.S.C. 154(b) by 667 days.

(21) Appl. No.: 11/881,846

(22) Filed: Jul. 31, 2007

(65) Prior Publication Data

US 2007/0298472 A1 Dec. 27, 2007

(51) Int. Cl.
*G01N 33/50* (2006.01)

(52) U.S. Cl. ............... 435/287.1; 204/400; 204/403.01; 204/403.04; 204/403.1; 204/403.14; 422/82.01; 435/287.2; 435/288.4; 435/817; 436/806

(58) Field of Classification Search .............. None
See application file for complete search history.

(56) References Cited

U.S. PATENT DOCUMENTS

| | | | |
|---|---|---|---|
| 4,352,885 | A | 10/1982 | Zeikus et al. |
| 5,126,034 | A | 6/1992 | Carter et al. |
| 5,216,034 | A | 6/1993 | Sie |
| 5,403,450 | A | 4/1995 | Mellor et al. |
| 5,976,719 | A | 11/1999 | Kim et al. |
| 6,270,649 | B1 | 8/2001 | Zeikus et al. |
| 6,495,023 | B1 | 12/2002 | Zeikus et al. |

FOREIGN PATENT DOCUMENTS

| | | |
|---|---|---|
| CA | 2340178 | 1/2000 |
| WO | WO 00/03447 | 1/2000 |

OTHER PUBLICATIONS

Boon, M. et al., "The ferrous iron oxidation kinetics of *Thiobacillus ferrooxidans* in continuous cultures", Appl. Microbiol Biotechnol (1999) 51: 820-826.
Ng, L-T. et al., "Natural polymer-based sulfite biosensor", Electroanalysis (1998) 10, No. 16: 1119-1124.
Mazuelos, A. et al., "High efficiency reactor for the biooxidation of ferrous iron", Hydrometallurgy (2000) 58: 269-275.
International Preliminary Examination Report for PCT/US02/17143 (International Filing Date May 31, 2002) dated Jan. 23, 2003.
International Search Report for PCT/US02/17143 (International Filing Date May 31, 2002) dated Dec. 2, 2002.

*Primary Examiner*—Christopher L Chin
(74) *Attorney, Agent, or Firm*—Ian C. McLeod; Steven M. Parks

(57) ABSTRACT

Electrodes and configurations for electrochemical bioreactor systems that can use electrical energy as a source of reducing power in fermentation or enzymatic reactions and that can use electron mediators and a biocatalyst, such as cells or enzymes, to produce electricity are disclosed. Example electrodes in the system may comprise: (1) neutral red covalently bound to graphite felt; (2) a carboxylated cellulose bound to the graphite felt, neutral red bound to the carboxylated cellulose, $NAD^+$ bound to the graphite felt, and an oxidoreductase (e.g., fumarate reductase) bound to the graphite felt; or (3) a metal ion electron mediator bound to graphite. Various biocatalysts, such as an oxidoreductase, cells of *Actinobacillus succinogenes*, cells of *Escherichia coli*, and sewage sludge, are suitable for use in the electrochemical bioreactor system.

21 Claims, 13 Drawing Sheets most oxidized metallic ions ●
more oxidized metallic ions ●
more reduced metallic ions ⊙
most reduced metallic ions ○

ELECTRODE COMPOSITIONS AND CONFIGURATIONS FOR ELECTROCHEMICAL BIOREACTOR SYSTEMS

CROSS-REFERENCES TO RELATED APPLICATIONS

This application claims the benefit of U.S. Provisional Patent Application No. 60/294,943 filed May 31, 2001, U.S. Provisional Patent Application No. 60/338,245 filed Nov. 8, 2001 and U.S. Provisional Patent Application No. 60/353,037 filed Jan. 30, 2002.

STATEMENT REGARDING FEDERALLY SPONSORED RESEARCH

Not Applicable.

BACKGROUND OF THE INVENTION

1. Field of the Invention

This invention relates to electrochemical bioreactor systems that can provide electrical enhancement of chemical synthesis and/or fermentations and/or biotransformations when supplied with electricity, that can generate electrical current detectable at a load, and that may used in chemical or biochemical sensing devices. In particular, the invention relates to improved electrodes for electrochemical bioreactor systems that can use electrical energy as a source of reducing power in fermentation or enzymatic reactions and that can use electron mediators and a biocatalyst, such as cells or enzymes, to produce electricity.

2. Description of the Related Art

A biofuel cell is a device that directly converts microbial metabolic power into electricity using electrochemical technology. (See, for example, Allen, "Cellular Electrophysiology", p. 247-283, In J. R. Norris and D. W. Ribbons (eds.). *Methods in Microbiology*. Academic Press, New York, 1992; Bennetto, et al. "The Sucrose Fuel Cell: Efficient Biomass Conversion Using A Microbial Catalyst", *Biotechnol. Lett.* 7:699-105, 1985; Roller et al., "Electron-Transfer Coupling In Microbial Fuel Cells: 1. Comparison Of Redox-Mediator Reduction Rates And Respiratory Rates Of Bacteria", *J. Chem. Tech. Biotechnol.* 34B:3-12, 1984; and Thurston, et al., "Glucose Metabolism In A Microbial Fuel Cell. Stoichiometry Of Product Formation In A Thionine-Mediated *Proteus Vulgaris* Fuel Cell And Its Relation To Coulombic Yields". *J. Gen. Microbial.* 131: 1393-1401, 1985.). Chemical energy is converted to electric energy by coupling the biodegradative oxidation of organic or inorganic substrates to the chemical reduction of an oxidant at the interface between the anode and the cathode (see, Willner et al. "A Biofuel Cell Based On Pyrroloquinoline Quinone And Microperoxidase-11 Monolayer-Functionalized Electrodes", *Bioelectrochem. Bioenerg,* 44:209-214, 1998.). Direct electron transfer from microbial cells to electrodes occurs at very low efficiencies (See, Allen, "Cellular Electrophysiology", p. 247-283, In J. R. Norris and D. W. Ribbons (eds.). *Methods in Microbiology*. Academic Press, New York, 1992). In microbial fuel cells, two redox couples are required, one for coupling reduction of an electron mediator to bacterial oxidative metabolism, and the other for coupling oxidation of the electron mediator to the reduction of the electron acceptor on the cathode surface where the electron acceptor is regenerated with atmospheric oxygen (see, Ardeleanu, et al., "Electrochemical Conversion In Biofuel Cells Using *Clostridium Butyricum* Or *Staphylococcus Aureus* Oxford", *Bioelectrochem. Bioenerg,* 11:273-277, 1983; and Delaney, et al., "Electron-Transfer Coupling In Microbial Fuel Cells. 2. Performance Of Fuel Cells Containing Selected Microorganism-Mediator-Substrate Combinations", *Chem. Tech. Biotechnol.* 34b:13-27, 1985).

Electron transfer from a microbial electron carrier to an electrode requires an electron mediator (See, Fultz et al., "Mediator Compounds For The Electrochemical Study Of Biological Redox Systems: A Compilation", *Anal. Chim. Acta.* 140:1-18, 1982.). Previous studies reported that metabolic reducing power produced by *Escherichia coli* or *Proteus vulgaris* was converted to electricity by using mediators such as 2-hydroxy-1,4-naphtoquinone (HNQ) or thionin (see, Tanaka et al., "Effects Of Light On The Electrical Output Of Bioelectrochemical Fuel-Cells Containing *Anabaena Varbilis* M-2: Mechanisms Of The Post Illumination Burst", *Chem. Tech. Biotechnol.* 42:235-240, 1988; and Tanaka et al., "Bioelectrochemical Fuel-Cells Operated By The Cyanobacterium, *Anabaena Variabilis*". *Chem. Tech. Biotechnol.* 35B: 191-197, 1985). Park et al. in "Electrode Reaction Of *Desulfovibrio Desulfuricans* Modified With Organic Conductive Compounds", *Biotech. Techniq.* 11:145-148, 1997 confirmed that viologen dyes (see, Kim et al., "Benzyl Viologen Cation Radical: First Example Of A Perfectly Selective Anion Ionophore Of The Carrier Type", *Biochem. Biophys. Res. Com.,* 180:11276-1130, 1982; and Morimyo, "Isolation And Characterization Of Methyl Viologen Sensitive Mutants Of *Escherichia Coli* K-12", *J. Bacteriol.* 170:2136-2142, 1988) cross-linked with carbon polymers and absorbed to *Desulfovivrio desulfuricans* cell membranes can mediate electron transfer to electrodes. Kim et al. in "Direct Electrode Reaction Of Fe(III)-Reducing Bacterium, *Shewanella Putrefacians, J. Microbial. Biotechnol.,* 9:127-13, 1999 showed that *Shawella putrefacians*, which contains outer-membrane cytochromes able to reduce $Fe^{3+}$, was electroactive and, that it could grow on lactate as the electron donor with a graphite felt electrode as the electron acceptor in a complex biofuel cell. U.S. Pat. No. 6,270,649 to Zeikus et al. shows that neutral red is an improved electron mediator for either converting electricity into microbial reducing power for enhanced cell growth and production of reduced end-products (see, Park et al., "Microbial Utilization Of Electrically Reduced Neutral Red And The Sole Electron Donor For Growth And Metabolite Production", *Appl. Environ. Microbiol.* 65:2912-2917, 1999; and Park et al., "Utilization Of Electrically Reduced Neutral Red By *Actinobacillus Succinogenes*: Physiological Function Of Neutral Red In Membrane-Driven Fumarate Reduction And Energy Conservation", *J. Bacteriol.* 1812:2403-2410, 1999), or converting microbial reducing power into electricity in biofuel cells (see, Park and Zeikus, "Electricity Generation In Microbial Fuel Cells Using Neutral Red And An Electronophore", *Appl. Environ. Microbiol.* 66:1292-1297, 2000). Park et al., in "Electricity Production In Biofuel Cell Using Modified Graphite Electrode With Neutral Red", *Biotech. Lett.* 22:1301-1304, 2000 showed that binding neutral red to a graphite electrode further enhanced electron transfer efficiency in microbial fuel cells.

The electrical enhancement of fermentations and biotransformations also involves the utilization of an electrode and electron mediator in a bioreactor system which overproduces reduced end products (see, Hongo et al., "Application Of Electro-Energizing Method To L-Glutamic Acid Fermentation", *Agri. Biolio. Chem.,* 43: 2075-20811 1979; Hongo et al., "Application Of Electro-Energizing Method To L-Glutamic Acid Fermentation", *Agri. Biolio. Chem.,* 43: 2083-2086, 1979; Kim et al., "Electron Flow Shift In

*Clostridium Acetobutylicum* Fermentation By Electrochemically Introduced Reducing Equivalent" 1988; Park and Zeikus "Utilization Of Electrically Reduced Neutral Red By *Actinobacillus Succinogenes*: Physiological Function Of Neutral Red In Membrane-Driven Fumarate Reduction And Energy Conservation", *J. Bacteriol.* 181: 403-2410, 1999; and Shin et al., "Evaluation Of An Electrochemical Bioreactor System In The Biotransformation Of 6-Bromo-2-Tetralone To 6-Bromo-2-Tetralol", *Appl Microbiol Biotechnol.*, DOI 10.1007/s002530100809. Online publication: Sep. 22, 2001.) For example, a graphite felt electrode and soluble neutral red can greatly enhance the yields of succinate produced by fermentation (see Park and Zeikus "Utilization Of Electrically Reduced Neutral Red By *Actinobacillus Succinogenes*: Physiological Function Of Neutral Red In Membrane-Driven Fumarate Reduction And Energy Conservation", *J. Bacteriol.* 181: 403-2410, 1999) and, tetralol produced by yeast transformation (Shin et al., "Evaluation Of An Electrochemical Bioreactor System In The Biotransformation Of 6-Bromo-2-Tetralone To 6-Bromo-2-Tetralol", *Appl Microbiol Biotechnol.*, DOI 10.1007/s002530100809. Online publication: Sep. 22, 2001). Neutral red works in part by direct chemical reduction of pyridine nucleotides (Park and Zeikus "Utilization Of Electrically Reduced Neutral Red By *Actinobacillus Succinogenes*: Physiological Function Of Neutral Red In Membrane-Driven Fumarate Reduction And Energy Conservation", *J. Bacteriol.* 181: 403-2410, 1999).

The use of oxidoreductases in microbial electrochemical cells has also been proposed. One major factor limiting the utilization of oxidoreductases in chemical syntheses (see, e.g., S. M. Roberts et al., Chimicaoggi, "Some Recent Advances In The Synthesis Of Optically Pure Fine Chemicals Using Enzyme-Catalyzed Reactions In The Key Step", July/August 1993, pp. 93-104; and D. Miyawaki et al., "Electrochemical Bioreactor With Immobilized Glucose 6-Phosphate Dehydrogenase On The Rotation Graphite Disc Electrode Modified With Phenazine Methosulfate", Enzg. Microbiol. Technol. 15:525-29, 1993) or in chemical detection, i.e., biosensors (see, e.g., P. N. Bartlett, "Modified Electrode Surface In Amperometric Biosensors", Med. and Biol. Eng. and Comput. 28: B10-B7, 1990; and D. Miyawaki et al., supra) is the lack of a facile system for regeneration or recycling of the electron transferring cofactors (e.g., nicotinamide adenine dinucleotide, quinones, flavin adenine dinucleotide, etc).

It has been reported by Park and Zeikus in "Utilization Of Electrically Reduced Neutral Red By *Actinobacillus Succinogenes*: Physiological Function Of Neutral Red In Membrane-Driven Fumarate Reduction And Energy Conversion", *J. Bacteriol.* 181:2403-2410, 1999 that neutral red would undergo reversible chemical oxidoreduction with nicotinamide adenine dinucleotide (i.e., recycle nicotinamide adenine dinucleotide electrochemically). It has also been reported that by using soluble neutral red in electrochemical reactors containing microbes that: (1) microbes could grow on electricity alone; (2) diverse microbes could over-produce a variety of reduced biochemicals during fermentations of biotransformations; and (3) microbes could generate electricity during digestion of organic matter. (See, e.g., Park et al., "Microbial Utilization Of Electrically Reduced Neutral Red In The Sole Electron Donor For Growth And Metabolite Production", *Appl. Environ. Microbiol.* pp. 2912-2917, 1990; Park and Zeikus, "Electricity Generation In Microbial Fuel Cells Using Neutral Red As An Electronophore", *Appl. Environ. Microbiol.*, 66:1292-1297, 2000; and U.S. Pat. No. 6,270,649).

Because of the importance of electrodes and electron mediators in bioreactor systems for electricity generation, chemical sensing, and electrical enhancement of chemical synthesis, fermentations and biotransformations, there is a continuing general need for improved electrodes that enhance the rate of electron transfer from cells. Preferably, the improved electrode compositions for increased electron transfer efficiency can use resting cells from pure and mixed bacterial cultures. In one specific application, there is a need for an improved electrode that has utility as an enzymatic fuel cell, as a sensor for succinate detection, and as an engineered catalyst for the synthesis of fumarate or succinate. In particular, there is a need for an enzyme immobilization protocol to link nicotinamide adenine dinucleotide (NAD), neutral red (NR), and fumarate reductase to an electrode in an electrochemical reactor.

Microbial electrochemical cells have previously used two-compartment systems whereby the aerated cathode compartment contains a chemical solution of ferric cyanide and oxygen, and the anode compartment contains bacterial cells, electron mediator, and reduced substrate (see, for example, Ardeleanu, et al., "Electrochemical Conversion In Biofuel Cells Using *Clostridium Butyricum* Or *Staphylococcus Aureus* Oxford", *Bioelectrochem. Bioenerg,* 11:273-277, 1983; and Park and Zeikus, "Electricity Generation In Microbial Fuel Cells Using Neutral Red And An Electronophore", *Appl. Environ. Microbiol.* 66:1292-1297, 2000). Two compartment fuel cells are generally not practical because of the requirement for a ferricyanide solution and aeration in the cathode compartment. Thus, there is also a need for a single compartment microbial electrochemical cell that eliminates the requirements for a ferricyanide solution and aeration in the cathode compartment.

SUMMARY OF THE INVENTION

The foregoing needs are met by an electrochemical bioreactor system according to the invention. The electrochemical bioreactor system comprises a first compartment containing a first electrode; a second electrode; an electrically conductive material connecting the first electrode and the second electrode; an electrolyte for providing ionic conductivity between the first electrode and the second electrode; and a biocatalyst disposed in the first compartment or associated with the first electrode.

When an electrical power supply, is electrically connected to the electrically conductive material and electrical current is applied from the electrical power supply to the first electrode and the second electrode, the first electrode acts as a cathode whereby the electrochemical bioreactor system provides electrical enhancement of chemical synthesis and/or fermentations and/or biotransformations occurring in the first compartment. When an electrical load (e.g., a resistive element) is electrically connected to the electrically conductive material, the first electrode acts as a anode and the electrochemical bioreactor system generates electrical current detectable at the load from materials in the first compartment. The electrical current detectable at the load may be used as a source of electricity, or measurement of the electrical current at the load may used in chemical or biochemical sensing devices.

In a first aspect of the invention, the first electrode of the electrochemical bioreactor system comprises graphite felt and at least one electron mediator associated with the graphite felt. As used herein, a first material (in the first aspect of the invention, an electron mediator) is "associated" with a second material (in the first aspect of the invention, graphite felt) if the first material is directly or indirectly, physically or chemically bound to the second material. A first material may be physically bound to a second material by entrapping, imbedding or otherwise containing the first material within the second material. A first material may be chemically bound to the second material by way of a chemical reaction wherein the first material is covalently or ionically bonded to the second material. Thus, various techniques for associating at least one electron mediator with the graphite felt are contemplated herein.

In one version of the first aspect of the invention, the first electrode comprises neutral red (NR) bound to the graphite felt. In another version of the first aspect of the invention, the first electrode comprises a carboxylated cellulose (e.g., carboxymethylcellulose) bound to the graphite felt and neutral red bound to the carboxylated cellulose. In yet another version of the first aspect of the invention, the first electrode comprises $NAD^+$ bound to the graphite felt. In still another version of the first aspect of the invention, the first electrode comprises a carboxylated cellulose bound to the graphite felt and $NAD^+$ bound to the carboxylated cellulose. In a further version of the first aspect of the invention, the first electrode comprises a carboxylated cellulose bound to the graphite felt, neutral red bound to the carboxylated cellulose, $NAD^+$ bound to the graphite felt, and an oxidoreductase (e.g., fumarate reductase) bound to the graphite felt. Each of these versions of the first electrode serves to enhance the rate of electron transfer from the biocatalyst.

In a second aspect of the invention, the first electrode of the electrochemical bioreactor system comprises a metal ion electron mediator. For example, the first electrode may comprise an iron cation (e.g., $Fe^{3+}$) and/or a manganese cation (e.g., $Mn^{4+}$) associated with a graphite plate. Each of these versions of the second electrode serves to enhance the rate of electron transfer from the biocatalyst.

Various biocatalysts are suitable for use in an electrochemical bioreactor system in accordance with the invention. For example, the biocatalyst may comprise an oxidoreductase (e.g., fumarate reductase) bound to the first electrode. The biocatalyst may also comprise bacterial cells disposed in the first compartment of the electrochemical bioreactor system. Non-limiting examples of bacterial cells include cells of *Actinobacillus succinogenes*, cells of *Escherichia coli*, and sewage sludge.

In a third aspect of the invention, the electrochemical bioreactor system is configured as a single compartment electrochemical cell. In the third aspect of the invention, the second electrode includes a first surface and a second opposed surface and the electrolyte is disposed on the first surface of the second electrode. The first surface faces an interior of the first compartment of the electrochemical bioreactor system and the second surface of the second electrode comprises an exterior surface of the first compartment of the electrochemical bioreactor system. The single compartment electrochemical cell design eliminates the requirements for a ferricyanide solution and aeration in the cathode compartment. When the single compartment electrochemical cell is used as an electricity generator, bacteria attach to the anode and electrons are transferred from the cells metabolic pool to reduce either neutral red or a metallic electron mediator immobilized on the anode. The electron driving force generated is coupled to reduction of Fe ions on the cathode which are subsequently oxidized by $O_2$ in the air. Consequently, a catholyte solution and % aeration are not required.

It is therefore an advantage of the present invention to provide an electrochemical bioreactor system having improved electrodes that enhance the rate of electron transfer from cells.

It is another advantage of the present invention to provide an electrochemical bioreactor system having an improved electrode that has utility as an enzymatic fuel cell.

It is yet another advantage of the present invention to provide an electrochemical bioreactor system having an improved electrode that has utility as a sensor for succinate detection.

It is still another advantage of the present invention to provide an electrochemical bioreactor system having an improved electrode that has utility as an engineered catalyst for the synthesis of fumarate or succinate.

It is a further advantage of the present invention to provide an electrochemical bioreactor system having an improved electrode with an enzyme immobilization protocol to link nicotinamide adenine dinucleotide ($NAD^+$), neutral red, and fumarate reductase to the electrode.

It is yet another advantage of the invention to provide a fuel cell system that can be used as either an enrichment device for electrophilic microorganisms; that is, those which use an electrode as an electron acceptor, or electron donor for energy conservation.

These and other features, aspects, and advantages of the present invention will become better understood upon consideration of the following detailed description, drawings, and appended claims.

DESCRIPTION OF THE DRAWINGS

FIG. 16 depicts the electrochemical reduction of $NAD^+$ to NADH by a Mn(IV)-graphite cathode and a Fe(III)-graphite anode. A 1 mM $NAD^+$ solution in Tris-HCL buffer (100 mM, pH 7.0) was the catholyte and a 200 mM $KH_2PO_4$ solution in deionized distilled water was the anolyte. Line 1 is the spectrum of 0.5 mN NADH; Line 2 is the spectrum of NADH reduced by the Mn(IV)-graphite electrode; and Line 3 is the spectrum of 1 mM $NAD^+$ that is not reduced by a normal graphite felt electrode.

DETAILED DESCRIPTION OF THE INVENTION

The present invention is directed to electrodes and configurations for electrochemical bioreactor systems that can use electrical energy as a source of reducing power in fermentation or enzymatic reactions and that can use electron mediators and a biocatalyst, such as cells or enzymes, to produce electricity. The electrochemical bioreactor system comprises a first compartment containing a first electrode; a second electrode; an electrically conductive material connecting the first electrode and the second electrode; an electrolyte for providing ionic conductivity between the first electrode and the second electrode; and a biocatalyst disposed in the first compartment or associated with the first electrode.

When an electrical power supply is electrically connected to the electrically conductive material and electrical current is applied from the electrical power supply to the first electrode and the second electrode, the first electrode acts as a cathode whereby the electrochemical bioreactor system provides electrical enhancement of chemical synthesis and/or fermentations and/or biotransformations occurring in the first compartment. When an electrical load (e.g., a resistive element) is electrically connected to the electrically conductive material, the first electrode acts as a anode and the electrochemical bioreactor system generates electrical current detectable at the load from materials in the first compartment. The electrical current detectable at the load may be used as a source of electricity, or measurement of the electrical current at the load may used in chemical or biochemical sensing devices.

Figure 1:
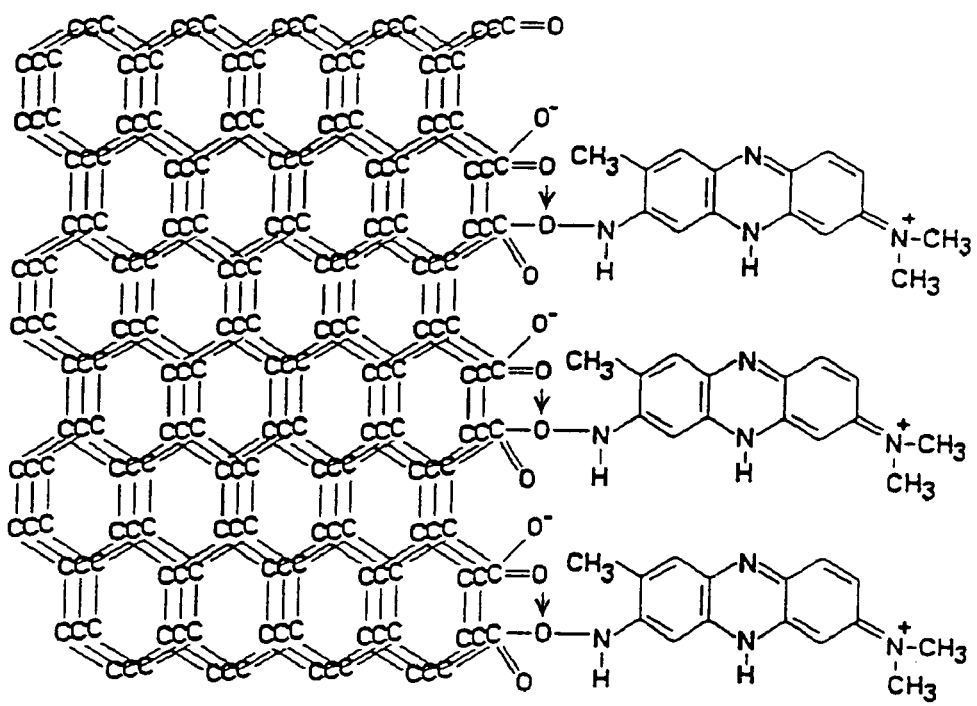
FIG. 1 is a schematic structure of a neutral red woven graphite electrode according to a first aspect of the invention. Neutral red was linked by a covalent bond between its amine and the carboxy of woven graphite.
Figure 2:
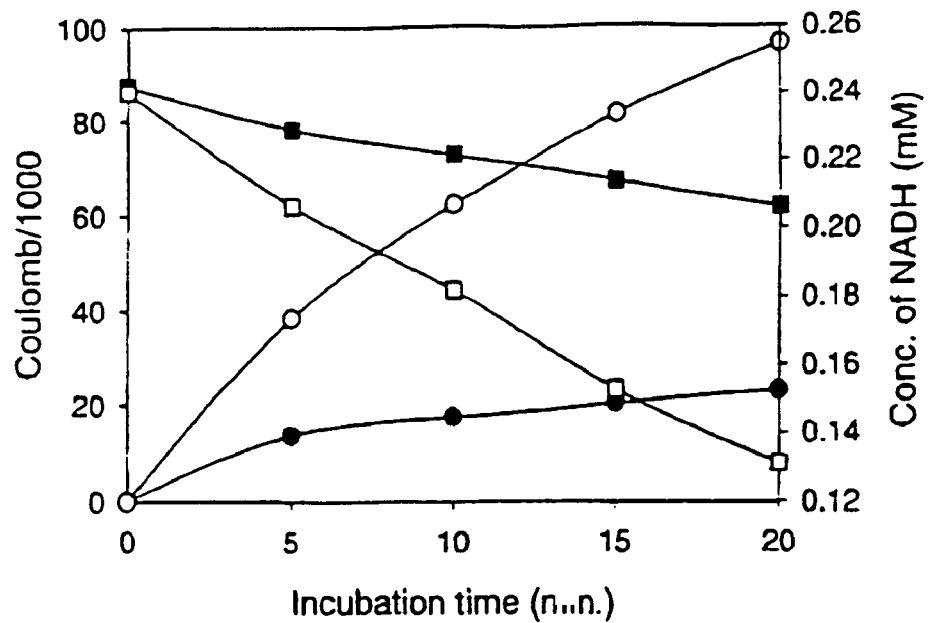
FIG. 2 shows the electricity production (in solid symbols) coupled to oxidation of NADH to $NAD^+$ on a normal electrode and electricity production coupled to oxidation of NADH to $NAD^+$ (in open symbols) on a modified electrode with Mn according to a second aspect of the invention. The theoretical efficiency of electricity production on the normal electrode and the modified electrode was 26.442% and 36.67%, respectively.

In one form, the first electrode comprises neutral red covalently bound to graphite felt. It has been discovered that the efficiency of electron transfer from microbial cells to electrodes can be increased by covalently linking neutral red to woven graphite felt. Neutral red can be covalently linked to graphite felt by converting at least a portion of the surface of the graphite felt to its carboxy form (using heat, for example) and covalently linking the amine group of neutral red to the carboxy of the woven graphite. FIG. 1 shows the covalent linking of neutral red to the graphite felt. The neutral red is immobilized on the graphite felt and does not leach-out in water.

The first electrode comprising neutral red covalently bound to graphite felt may then be incorporated into an electrochemical bioreactor system using known methods within the ability of one skilled in the art. A typical electrochemical bioreactor system will include two compartments, each of which contains one of the first and the second electrodes. The second electrode may comprise an iron cation (e.g., $Fe^{3+}$) associated with a graphite plate. The electrodes are separated by an ionically conductive electrolyte material between the first electrode and the second electrode. Typically, the electrolyte allows for the passage of protons and cations only. Solid electrolyte materials are well known and include materials such as Nafion™ cationic selective membranes and porcelain septums. Catholytes and anolytes may also be used in the compartments. For example, catholytes and anolytes that have been found to be suitable in electrochemical bioreactors include bacterial growth media or a phosphate buffer. The electrodes can be connected to an electrical power source or to a multimeter (or other resistive load) using an electrically conductive material such as a metallic material (e.g., platinum wire). A suitable biocatalyst is disposed in the compartment containing the first electrode or is associated (as defined above) with the first electrode.

A wide range of biocatalysts to promote cell growth or the formation of reduced products in the electrochemical bioreactor system can be used. For example, a wide variety of bacteria, archea, plant cells or animal cells can be used. Non-limiting examples include cells of *Actinobacillus succinogenes*, cells of *Escherichia coli*, and sewage sludge. Enzyme preparations may also be used in the practice of the invention. A desired enzyme may be partially purified using standard methods known to one of ordinary skill in the art. The enzyme may be isolated from its native source or from a transgenic expression host, or obtained through a commercial vendor. Useful enzymes include any enzyme that can use reducing power from an electron mediator to form a desired reduced product, or which can transfer reducing power to an electron mediator and form a desired oxidized product. Most commonly, this reduction is mediated by NADPH or NADH. An oxidoreductase may be used as the biocatalyst in the practice of the invention. For example, isolated alcohol dehydrogenases, carboxylic acid reductase, and fumarate reductase could be used in the electrochemical bioreactor system.

In another form, the first electrode of the electrochemical bioreactor system comprises a metal ion electron mediator. For example, the first electrode may comprise an iron cation (e.g., $Fe^{3+}$) and/or a manganese cation (e.g., $Mn^{4+}$) associated with a graphite plate. The first electrode comprising the metal ion electron mediator may be incorporated into an electrochemical bioreactor system using known methods as described above.

The present invention also provides a method for utilizing oxidoreductase as biocatalysts for chemical sensing and chemical production, and as a biofuel cell by immobilizing on an electrode an oxidoreductase and multiple electron carriers such as nicotinamide adenine dinucleotide ($NAD^+$) and neutral red (NR) which can be bioelectrically regenerated. In one version of the invention, fumarate reductase enzyme is immobilized onto a graphite felt electrode that is modified with carboxymethylcellulose (CMC), neutral red (NR) and nicotinamide adenine dinucleotide ($NAD^+$). The fumarate reductase enzyme is immobilized onto a CMC-NR-$NAD^+$ modified graphite felt electrode by preparing fumarate reductase, preparing a graphite electrode substrate, treating the electrode with neutral red, treating the electrode with carboxymethylcellulose, treating the electrode with $NAD^+$, and treating the electrode with the fumarate reductase to produce a CMC-NR-$NAD^+$-fumarate reductase modified electrode.

Figure 10:
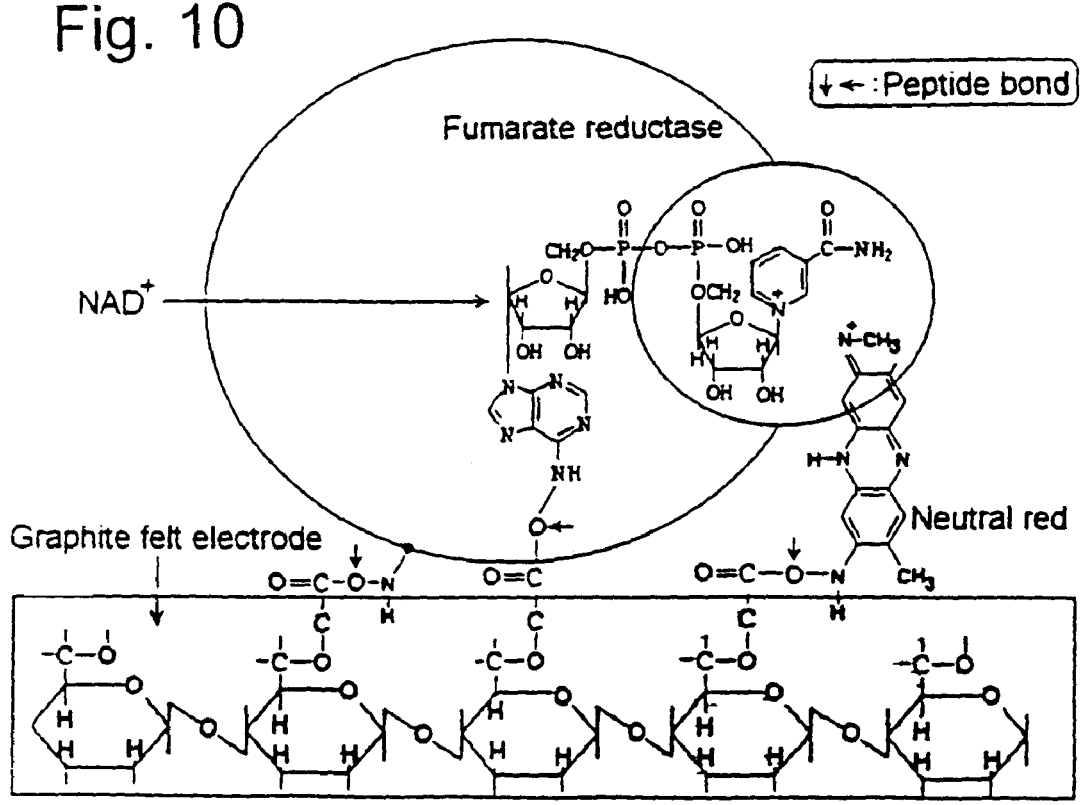
FIG. 10 is a schematic diagram showing a graphite felt electrode modified with CMC-NR-$NAD^+$-fumarate reductase complex according to the invention.

Looking at FIG. 10, there is shown schematically a graphite felt electrode with a CMC-NR-$NAD^+$-fumarate reductase complex according to the invention. The chemical linkings between carboxymethylcellulose, $NAD^+$, fumarate reductase and neutral red on the graphite electrode are depicted in FIG. 10. The CMC-NR-$NAD^+$-fumarate reductase complex is a thin film on the electrode. The graphite felt electrode is modified with neutral red before coating with the CMC-NR-$NAD^+$-fumarate reductase complex. The electrons can be reversibly transferred from the graphite felt to the fumarate reductase or from the fumarate reductase to the graphite felt by the coupling oxidation-reduction reaction of neutral red and $NAD^+$. The coupling oxidation-reduction reaction of neutral red and $NAD^+$ provides a mechanism by which fumarate can be reduced to succinate thereby consuming electricity and succinate can be oxidized to fumarate thereby producing electricity.

Figure 9:
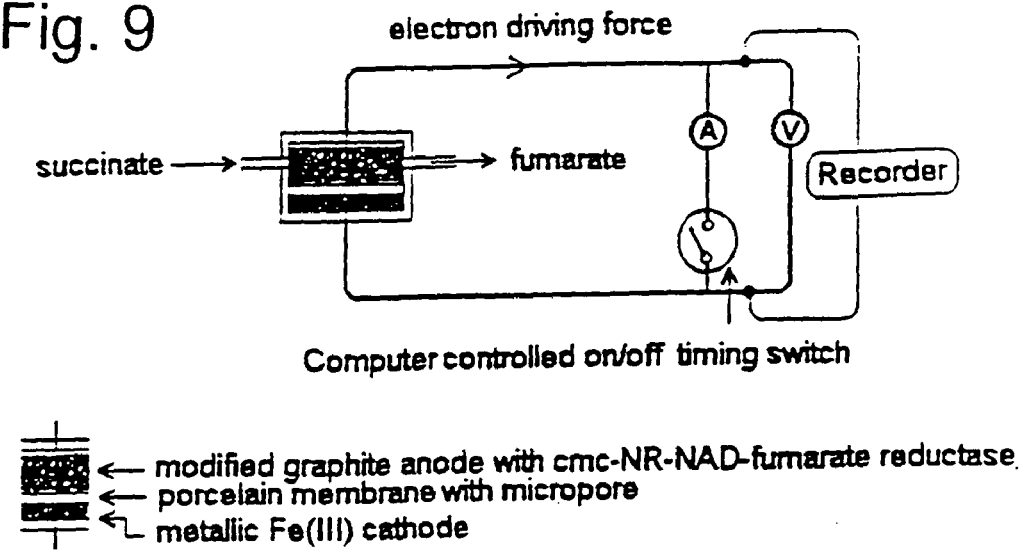
FIG. 9 is a schematic diagram showing one compartment of a bioelectrochemical cell using a graphite felt electrode modified with CMC-NR-$NAD^+$-fumarate reductase complex according to the invention.

The CMC-NR-$NAD^+$-fumarate reductase electrode may be incorporated into an electrochemical bioreactor system for chemical sensing, chemical production and electricity production as shown schematically in FIG. 9. FIG. 9 illustrates an electrochemical bioreactor system that may be used for succinate detection or fumarate synthesis. The anode contains fumarate reductase, $NAD^+$, and neutral red immobilized on a graphite electrode with carboxymethylcellulose according to the invention.

Figure 11:
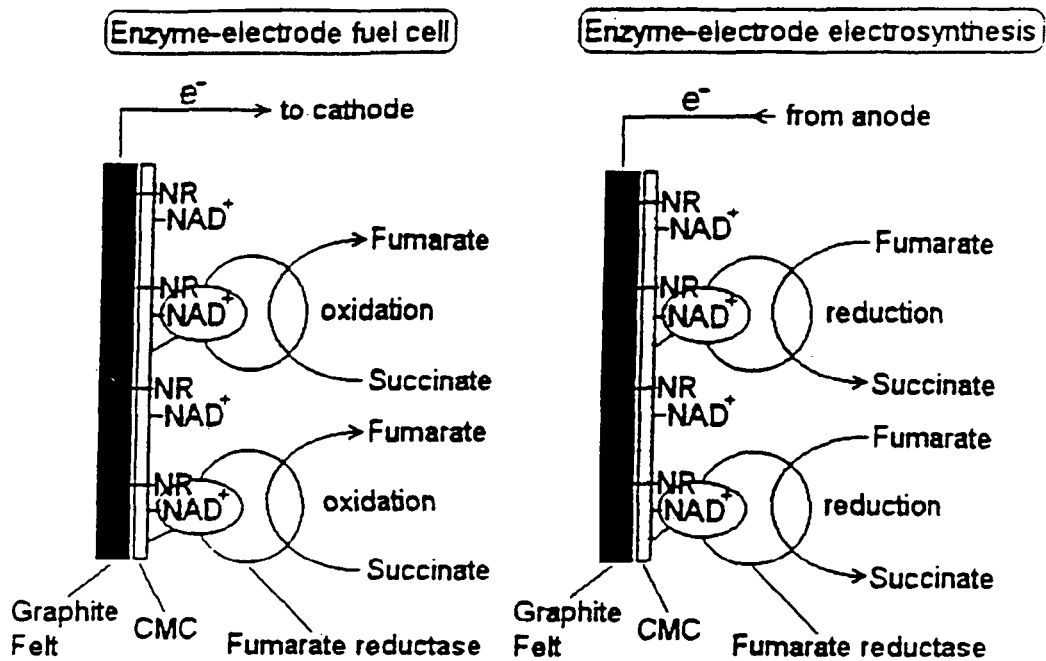
FIG. 11 is a schematic diagram showing the mechanisms for oxidation of succinate to fumarate coupled to electricity production and the reduction of fumarate to succinate coupled to electricity consumption using an electrode modified with CMC-NR-$NAD^+$-fumarate reductase complex according to the invention.

Turning to FIG. 11, there is shown a schematic that depicts how the CMC-NR-$NAD^+$-fumarate reductase enzyme immobilized onto the graphite felt electrode can function as a fuel cell during succinate oxidation and as a catalyst producing succinate from electricity and fumarate. The oxidation of succinate to fumarate coupled to electricity production and the reduction of fumarate to succinate coupled to electricity consumption is catalyzed by fumarate reductase which is bound to carboxymethylcellulose with $NAD^+$ and neutral red. The graphite felt electrode is coated with the CMC-NR-$NAD^+$-fumarate reductase complex. The neutral red, $NAD^+$ and the fumarate reductase can be covalently bonded to the carboxy residues of both the graphite felt and the carboxymethylcellulose.

The fumarate reductase is used as a oxidoreductase for the continuous enzymatic reduction-oxidation during bioelectrochemical synthesis or the detection of chemicals. When the fumarate reductase enzyme is immobilized onto a graphite felt electrode that is modified with carboxymethylcellulose (CMC), neutral red (an electron mediator) and nicotinamide adenine dinucleotide, the detection of succinate with this bioelectrode is linear from a lower level of 5 mM to 10 mM. The synthesis of fumarate using this bioelectrode is dependent on succinate utilization and results in a proportional amount of electricity and fumarates produced. The synthesis of succinate using the bioelectrode is also dependent on current and fumarate concentration. This electrochemical bioreactor system can enhance the utility of oxidoreductases in diverse enzymatic fuel cells, chemical synthesis and chemical detection.

Figure 3:
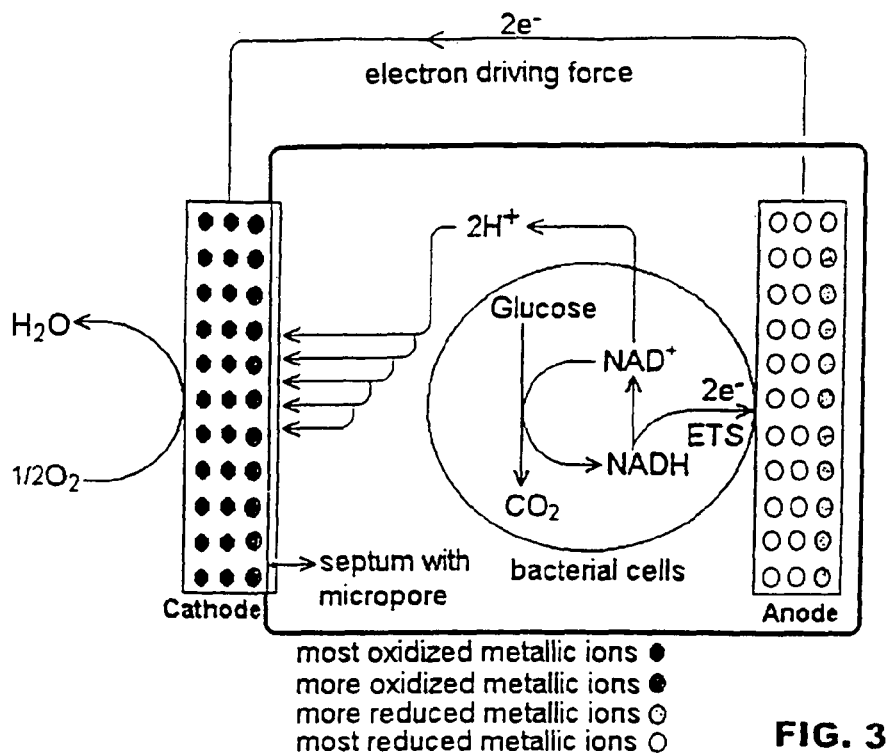
FIG. 3 is a schematic diagram of a single compartment fuel cell according to a third aspect of the invention depicting electron transfer from cell metabolism to the anode metals to the cathode metals; and, proton transfer through the porcelain septum to water. The electron driving force is produced by the potential difference between the most oxidized metallic ion in the anode to the most reduced metallic ion in the cathode.
Figure 4:
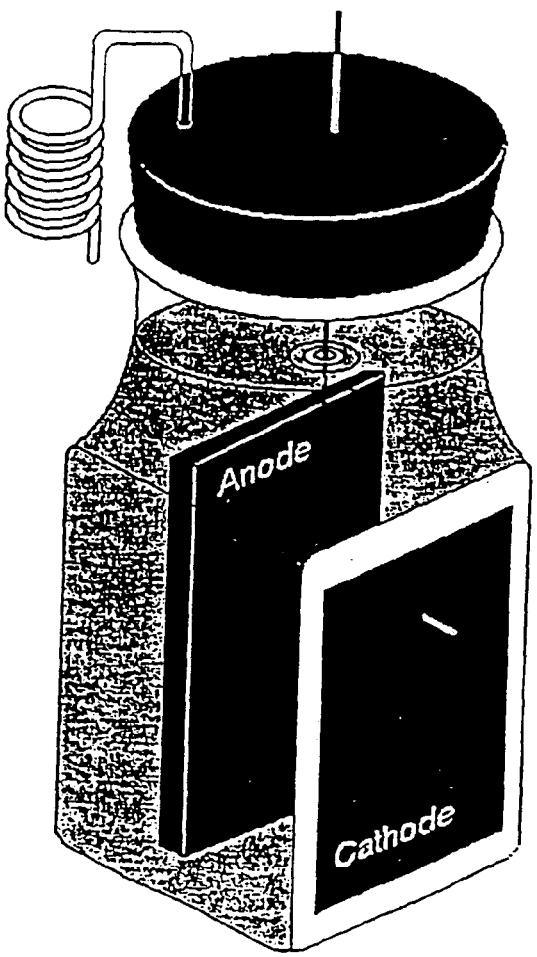
FIG. 4 is a diagrammatic representation of the single compartment fuel cell of FIG. 3. The single compartment fuel cell comprises a Pyrex™ glass container (total volume 500 ml.) with a $Fe^{3+}$ cathode (50 cm² surface area) and a rubber bung with a connected $Mn^{4+}$ graphite anode and an $N_2$ gassing port.

It has been discovered that the above electrodes can be incorporated into a single compartment electrochemical bioreactor system according to the invention. The single compartment electrochemical bioreactor system is shown in FIGS. 3 and 4. FIG. 3 provides a schematic of how the single compartment fuel cell works. Bacteria attach to the anode and electrons are transferred from the cells metabolic pool to reduce either neutral red or a metallic electron mediator immobilized on the anode. The electron driving force generated is coupled to reduction of Fe ions on the cathode which are subsequently oxidized by $O_2$ in air. Thus, a catholyte solution and aeration is not required. Protons are transferred from the anolyte solution through the micropore system on the cathode.

EXAMPLES

The following examples serve to further illustrate the invention. The examples are not intended to limit the invention in any way.

Example 1

Microbial Preparations and Measurements

Sewage sludge (i.e., a mixture of anaerobic bacteria) was obtained from the Jackson, Mich., USA, sewage treatment plant. The fresh anaerobic sludge was allowed to settle under an $N_2$ atmosphere for 1 day to remove solid particles. The suspended cells were used as a catalyst and were maintained in an anaerobic bottle by adding glucose (5 g/L) once a week. The resting cells were harvested by centrifugation at 5,000×g at 4° C. and were washed twice and resuspended in anolyte medium 1. Anolyte medium I contained: 100 mM phosphate buffer (pH 7.0), 10 g/L sodium lactate, 5 g/L peptone and 5 g/L yeast extract. The initial concentration of sewage sludge cell suspension was adjusted to 5.5 mg/ml cell protein as determined (see, Park and Zeikus, "Utilization Of Electrically Reduced Neutral Red By *Actinobacillus Succinogenes*: Physiological Function Of Neutral Red In Membrane-Driven Fumarate Reduction And Energy Conservation", *J. Bacteriol.* 1812:2403-2410, 1999) using Bradford reagent and bovine serum albumen as standard.

*Escherichia coli* K12 was grown anaerobically under $N_2$ gas for 20 hours to the stationary phase in an LB medium which contained: 10 g/L peptone, 5 g/L yeast extract and 10 g/L NaCl. The resting cells were harvested at 4° C. by centrifugation at 5,000×g. The resting cells were washed twice and resuspended in Anolyte medium I at an optical density of 3.5 at 660 nm which corresponded to a 4.73 mg/ml cell protein.

Example 2

Electrode Compositions

A procedure to covalently link neutral red to woven graphite felt was developed (see FIG. 1). The theoretical surface area of the woven graphite felt anode is 1.27 $m^2$ (2.7 g) versus a graphite plate anode with approximately 80 $cm^2$. This procedure involved the following steps: (1) cleaning the graphite felt electrode by soaking in methanol for 12 hours and then distilled water for 12 hours; (2.) drying the electrode at 120° C. for 1 hour; (3) making a carboxy surface by heating at 200° C. for 48 hours; (4) soaking the electrode in dicyclohexylcarbodimide solution (2 mg/ml chloroform) at 4° C. for 6 hours; (5) binding neutral red (100 μmol) to the electrode by incubating the dicyclohexylcarbodimide solution at 4° C. for 12 hours. The neutral red was immobilized to the electrode by this procedure and did not leach-out in water.

Several different metallic graphite electrodes were designed so as to compare their electron transfer efficiencies to neutral red-graphite felt. A ferric ($Fe^{+3}$) graphite electrode was made by mixing ferric sulfate (3% w/w) with 60% (w/w) fine graphite powder (below 500 mesh), 36% (w/w) kaolin (porcelain) with a particle size below 400 mesh and 1.0% (w/w) nickel chloride. One part distilled water and 2 parts of this mixture were stirred into a paste and molded into a 20 cm×20 cm×1 cm thick plate by pressing at 1.0 kg/$cm^2$, drying in air for 48 hours at room temperature, and then baking at 1100° C. for 12 hours in a kiln kept anaerobic with a flow of $N_2$ gas. A $Mn^{+4}$ graphite electrode was made in the same manner except 3% w/w manganese sulfate replaced the ferrous sulfate.

The cathodes differed from the anodes in the single compartment fuel cell because the inside of the cathode was coated with a 1 millimeter thickness porcelain septum made from 100% kaolin. The porcelain septum enabled protons to transfer from the anolyte to the cathode.

Example 3

Fuel Cell Design and Operation

Two compartment cell fuel cells were prepared using the configuration described in Park and Zeikus, "Electricity Generation In Microbial Fuel Cells Using Neutral Red And An Electronophore", *Appl. Environ. Microbiol.*, 66:1292-1297, 2000, except for using the electrodes prepared in Example 2; and the cation selective membrane was replaced with a 50 mm by 2 mm thick porcelain septum made from 100% Kaolin as described above in Example 2. The two compartment fuel cell of Park and Zeikus, "Electricity Generation In Microbial Fuel Cells Using Neutral Red And An Electronophore", *Appl. Environ. Microbiol.*, 66:1292-1297, 2000 requires aeration and ferricyanide solution in the cathode compartment.

Because two compartment fuel cells are generally not practical because of the requirement for a ferricyanide solution and aeration in the cathode compartment, single compartment fuel cell design as shown in FIGS. 3 and 4 was prepared in order to eliminate the requirements for a ferricyanide solution and aeration in the cathode compartment. FIG. 3 provides a schematic of how the single compartment fuel cell works. Bacteria attach to the anode and electrons are transferred from the cells metabolic pool to reduce either neutral red or a metallic electron mediator immobilized on the anode. The electron driving force generated is coupled to reduction of Fe ions on the cathode which are subsequently oxidized by $O_2$ in the air. Consequently, a catholyte solution and aeration is not required. Protons are transferred from the anolyte solution through the micropore system on the cathode. A $Mn^{4+}$ graphite anode and an $Fe^{3+}$ graphite cathode achieved the highest level of current (i.e. ~14 nA) using sewage sludge microbes. This was four-fold higher than the best *E-coli* value obtained and, it was three-fold higher than what was previously described for sewage sludge using soluble neutral red and a plain, woven graphite electrode (See, Park and Zeikus, "Electricity Generation In Microbial Fuel Cells Using Neutral Red And An Electronophore", *Appl. Environ. Microbiol.*, 66:1292-1297, 2000).

Resting cell suspensions in anolyte medium I were placed in the anoxic anode compartment of the two versus one compartment fuel cell systems and electrical current and potential were measured as reported in Park and Zeikus, "Electricity Generation In Microbial Fuel Cells Using Neutral Red And An Electronophore", *Appl. Environ. Microbiol.*, 66:1292-1297, 2000. Experiments compared electrical performance of *E. coli* versus sewage sludge in two versus one compartment fuel cells that contained different electrode compartments for the anode and cathode. The electrical measurements used a joule as the unit of energy which was calculated using the equation; ampere (A) times volt (V) times time (sec). A coulomb is equal to A times sec, and a coulomb times V is equal to a joule. Thus, a joule represents the amount of electrons (amperes) with a driving force (volts) in a closed circuit system per time unit. For calculations of the joule value, the current, potential and time were all measured in the fuel cells employed.

Example 4

Single Compartment Fuel Cell

Electricity Production by *E. coli*

Figure 5:
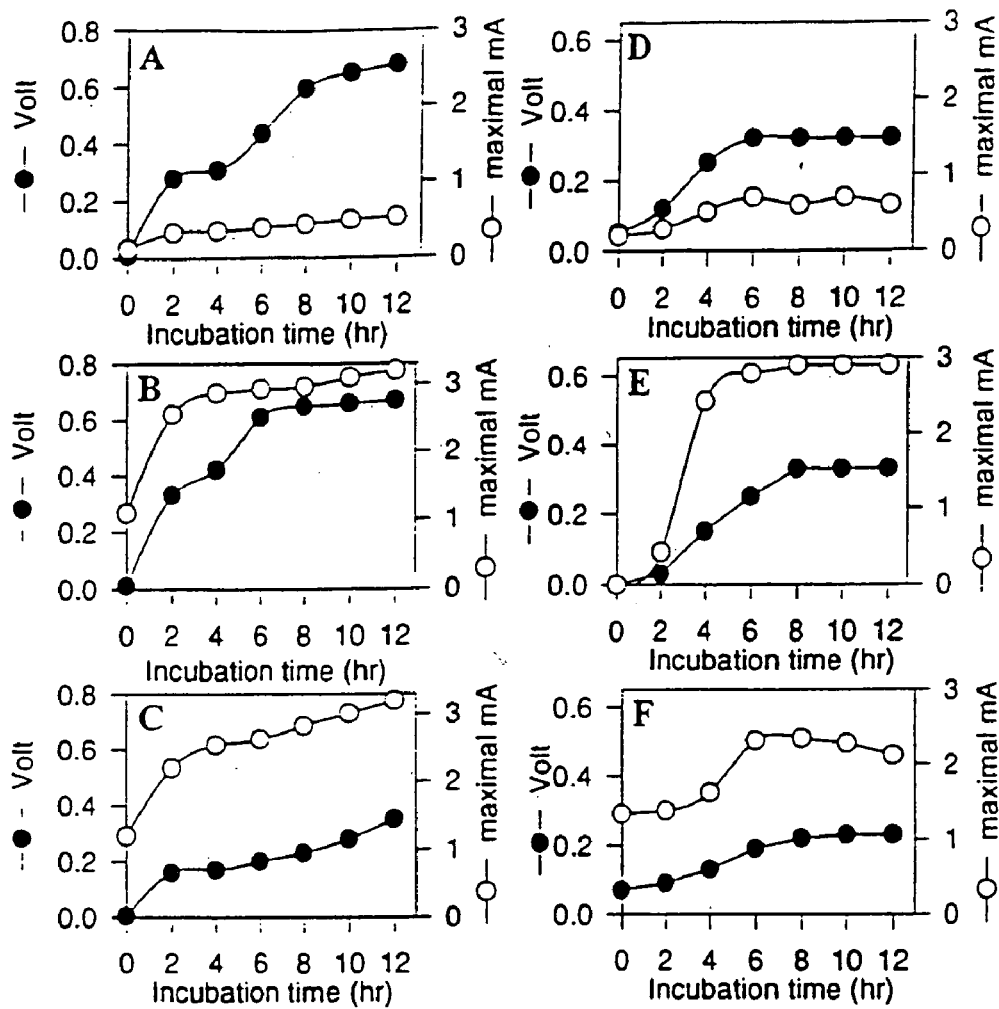
FIG. 5 is a comparison of electrical current and potential levels obtained when *Escherichia coli* was used in a two compartment fuel cell (A, B and C) versus a single compartment fuel cell (D, E and F). Three different types of anode and cathode combinations were applied to each fuel cell system. (A) and (D) were a woven graphite anode and a $Fe^{3+}$ graphite cathode; (B) and (E) were a neutral red woven graphite anode and a $Fe^{3+}$ graphite cathode; and (C) and (F) were a $Mn^{4+}$ graphite anode and a $Fe^{3+}$ graphite cathode.

FIG. 5 compares electricity generation by *E. coli* in a two compartment fuel cell as prepared as described above (A, B and C) versus a single compartment fuel cell as prepared as described above (D, E, and F) with different electrode compositions. Potential was higher in the two compartment fuel cell; whereas current was equivalent in either fuel cell system. Current was significantly lower when a woven graphite anode and a $Fe^{3+}$ graphite cathode were used. Notably, nearly equivalent current levels were obtained when either a neutral red woven graphite anode or a $Mn^{+4}$ graphite anode were used as electrodes in either fuel cell system with a $Fe^{3+}$ graphite cathode.

Table A summarizes the comparison of electricity production by *Escherichia coli* with different anode-cathode combinations. *E. coli* produced increasing levels of current using $Fe^{+3}$ graphite as the cathode when the anode was charged from graphite woven to NR-graphite woven to $Mn^{+4}$ graphite. The electron transfer efficiency with *E. coli* was dramatically higher with $Mn^{+4}$ graphite as the anode. When comparing electrical production *E. coli* using the neutral red-woven graphite electrode developed here versus the system described in Park and Zeikus, "Electricity Generation In Microbial Fuel Cells Using Neutral Red And An Electronophore", *Appl. Environ. Microbiol.*, 66:1292-1297, 2000 using soluble neutral red and a woven graphite as the anode, there was observed a maximum potential of 0.85 volt and a maximum current of 3.9 mA/12 g woven graphite (3.14 mA/m$^2$ graphite electrode) with soluble neutral red; and, a maximum potential of 0.79 volt maximum current and 17.7 mA/2.7 g woven graphite (3.0 m A/m$^2$ graphite electrode with neutral red linked woven graphite electrode). The electron transfer of neutral red linked to woven graphite was 10-fold higher than neutral red linked to a graphite plate reported by Park et al., in "Electricity Production In Biofuel Cell Using Modified Graphite Electrode With Neutral Red", *Biotech. Lett.* 22:1301-1304, 2000.

Example 5

Electricity Production by Sewage Sludge

Figure 6:
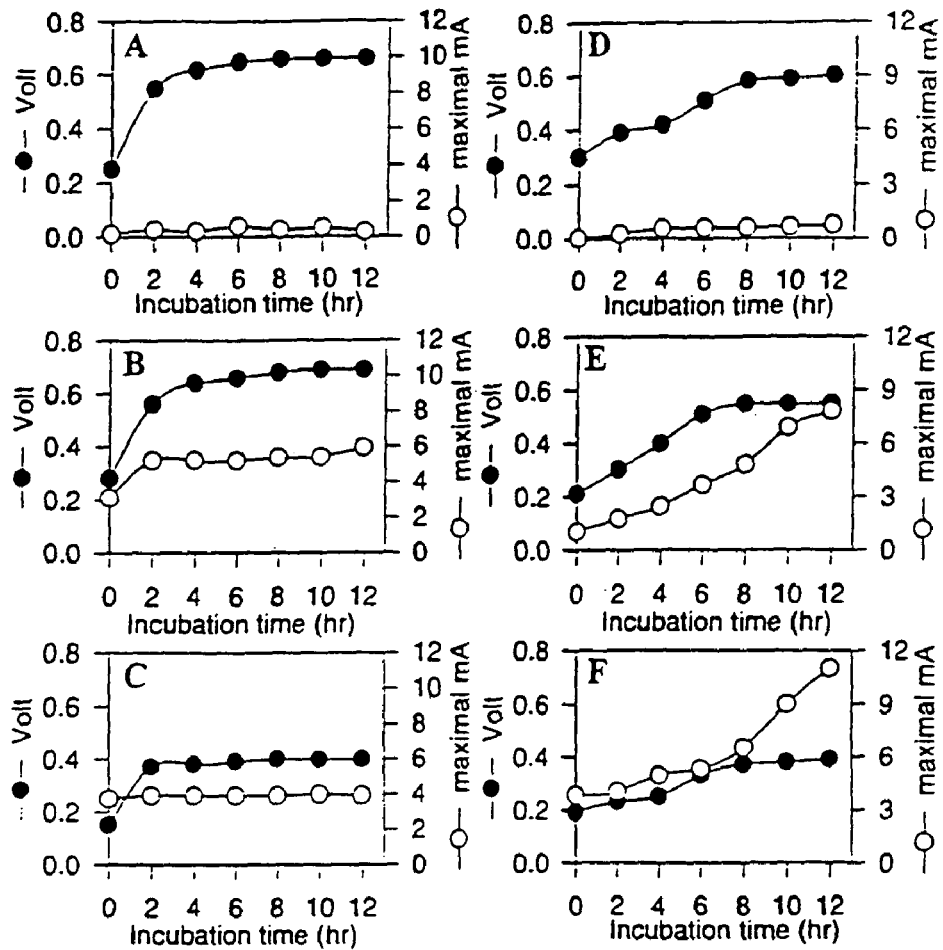
FIG. 6 is a comparison of electrical current and potential levels obtained when sewage sludge was used in a two compartment fuel cell (A, B and C) versus a single compartment fuel cell (D, E and F). Three different types of anode and cathode combinations were applied to each fuel cell system. (A) and (D) were a woven graphite anode and a $Fe^{3+}$ graphite cathode; (B) and (E) were a woven graphite anode with neutral red and a $Fe^{3+}$ graphite cathode; and (C) and (F) were a $Mn^{4+}$ graphite anode and a $Fe^{3+}$ graphite cathode.

FIG. 6 compares electricity production by sewage sludge microbes in a two compartment fuel call as prepared above (A, B, C) versus a one compartment fuel cell as prepared above (D, E, F). Current was higher in the single compartment fuel cell than the two compartment fuel cell with all anode-cathode combinations tested; whereas, the potential was nearly equivalent. Sewage sludge bacteria produced significantly higher current levels than *E. coli* for all anode-cathode combinations that were tested (see Table A).

Figure 7:
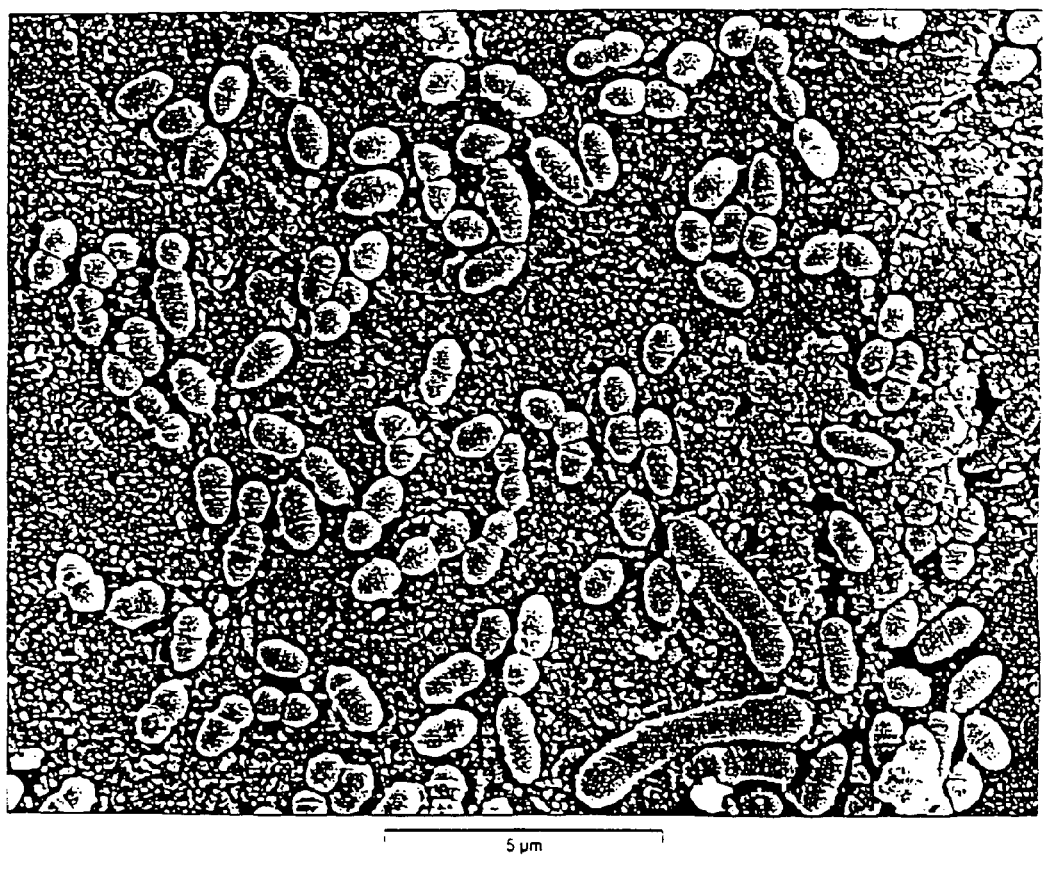
FIG. 7 is a scanning electron microscope photograph of grazing microbes attached to a neutral red-woven graphite anode. These electrogenic microbes were predominantly cocci that were enriched from sewage sludge.

After the experiments were finished, the anode was removed from the one compartment fuel cell and examined it by scanning electron microscopy (see FIG. 7). Sample preparation and scanning electron microscopy investigation were performed at Michigan State University Center for Advanced Microscopy, East Lansing, Mich., USA. The graphite felt was removed at the end of the experiment in the fuel cell containing sewage sludge and glucose. The graphite felt electrode sample (cut from electrode surface 5×5×5 mm) was fixed in 4% glutaraldehyde buffered with 0.1 M sodium phosphate at pH 7.4. Following a brief rise in the buffer, the sample was dehydrated in ethanol an series (24%, 50%, 75%, 95%) for 5 minutes at each gradation and with 3-5 minute changes in 100% ethanol. The sample was then critical point dried in a Blazers critical point dryer, with liquid carbon dioxide as the transitional fluid. The sample was then mounted on the aluminum stab using epoxy glue and sputter coated with gold in an Emscope Sputter Coater SC500 purged with argon gas. The sample was then examined in a JEOL JSM-6400V scanning electron microscope. The electrode surface was covered primarily with a coccoidial morphological type of bacteria. The diversity of different morphological types observed on the electrode surface was greatly limited from that observed in the sewage sludge itself. Apparently specific bacteria attached to the anode and used it as an electron acceptor for growth and energy metabolism.

TABLE A

Comparison of electricity production among four anode-cathode combinations in biofuel cell systems with resting cells of anaerobic sewage sludge or *E. coli* as biocatalyst.

| | | | The mean of electricity production | | |
|---|---|---|---|---|---|
| Biocatalyst (bacteria) | Anode Materials | Cathode Materials | Current (mA) | Potential (V) | Approximate Electron Transfer Efficiency (mA/m$^2$ electrode$^c$) |
| Sewage Sludge | Woven Graphite$^a$ | Woven Graphite$^a$ | 0.34 | 0.6 | 0.268 |
| | Woven Graphite | $Fe^{3+}$ Graphite | 1.30 | 0.6 | 1.024 |
| | NR Woven Graphite$^b$ | $Fe^{3+}$ Graphite | 11.0 | 0.58 | 8.661 |
| | $Mn^{4+}$ Graphite | $Fe^{3+}$ Graphite | 14.0 | 0.45 | 1750 |
| *E. Coli* | Woven Graphite$^a$ | Woven Graphite$^a$ | 0.6 | 0.6 | 0.47 |
| | Woven Graphite | $Fe^{3+}$ Graphite | 1.5 | 0.35 | 1.181 |

TABLE A-continued

Comparison of electricity production among four anode-cathode combinations in
biofuel cell systems with resting cells of anaerobic sewage sludge or *E. coli* as biocatalyst.

| Biocatalyst (bacteria) | Anode Materials | Cathode Materials | The mean of electricity production | | Approximate Electron Transfer Efficiency (mA/m$^2$ electrode[c]) |
|---|---|---|---|---|---|
| | | | Current (mA) | Potential (V) | |
| | NR Woven Graphite[b] | Fe$^{3+}$ Graphite | 3.3 | 0.35 | 2.598 |
| | Mn$^{4+}$ Graphite | Fe$^{3+}$ Graphite | 2.6 | 0.28 | 325 |

[a]Two compartment system used for combination of graphite-graphite electrodes.
[b]Modified graphite woven electrode with covalently linked neutral red bond.
[c]This is a theoretical value obtained by calculation using the electrode surface area used in the biofuel cell system but it is not an experimental value. The external shape and size of the three electrodes was the same but the weight and surface areas were different.

Analysis of Examples 1-5

Practical improvements have been demonstrated in both microbial fuel cell designs and enhanced microbial electron transfer efficiencies with new cathode and anode compositions. The new single compartment fuel cell system offers advantages over a conventional two compartment fuel cell. First, the new single compartment fuel cell system is simpler and less expensive to construct and operate, Second, the single compartment fuel cell system eliminates the need for a ferricyanide catholyte and aeration which might use more energy than the fuel cell makes, Third; the single compartment fuel cell system replaces the expensive proton selective membrane with a porcelain septum. Fourth, the use of a Fe$^{+3}$ graphite cathode enhances electron transfer efficiency for a wide range of microbes as potential biocatalysts. A current of 14 mV was produced with sewage sludge using Mn$^{4+}$ graphite anode and a Fe$^{3+}$ cathode which is three times higher than reported using a woven graphite electrode and soluble neutral red (See, Park et al., "Electricity Production In Biofuel Cell Using Modified Graphite Electrode With Neutral Red", *Biotech. Lett.* 22:1301-1304, 2000.).

Figure 8:
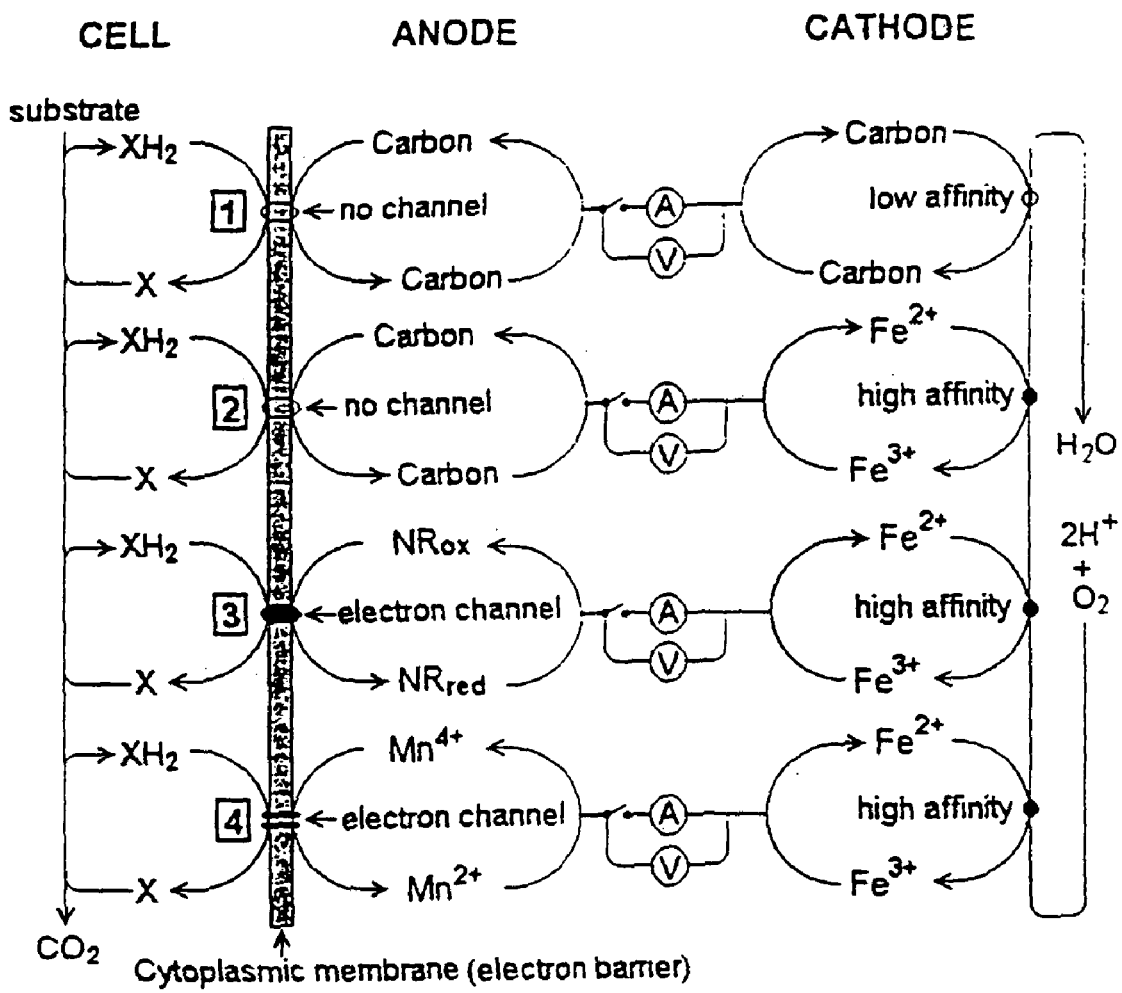
FIG. 8 is a schematic diagram for depicting electricity generation on different electrode combinations during electron transfer from microbes to oxygen and protons via the anode (left) to the cathode (right). In System 1, the electrons are difficult to transfer from the microbial cells to the anode, the cathode, and oxygen because there is neither an electron channel (i.e. an electron mediator), nor a high oxygen affinity metallic ion in the cathode. Consequently, the current obtained in System 1 is low but the potential difference between the anode and cathode is high. In System 2, the electrons are difficult to transfer from the microbes to the anode but are easier to transfer from the cathode to oxygen because of $Fe^{3+}$; thus, the current produced is higher than System 1 but the potential is similar. In System 3, the electrons are easy to transfer from the microbes to the anode and cathode because of neutral red and $Fe^{3+}$; thus, the current is higher but the potential is lower in System 1 or 2. In System 4, the electrons are very easy to transfer from the microbes to the anode and cathode because of $Mn^{4+}$ as an electron mediator and $Fe^{3+}$ as a high oxygen affinity ion; thus, the current obtained is higher than in System 1 or 2, but the potential is lower than in System 1, 2 or 3 because the potential difference between $Mn^{4+}$ and $Fe^{3+}$ is lower than between neutral red and $Fe^{3+}$ or no electron mediator and $Fe^{3+}$. The $E_o'$ value (in volts) for electron mediators are: neutral red −0.325; Mn +0.35: Fe, +0.78; and $O_2$, +0.82. The cytoplasmic membrane functions are an electron barrier providing resistance to electron transfer which can be overcome by adding neutral red or $Mn^{4+}$ which serves as an electron mediator or channel.

FIG. 8 provides a diagrammatic explanation for the different potential and current levels obtained when different anode and cathode configurations were used to produce electricity in microbial fuel cells using either *E. coli* or anaerobic sewage sludge. In general, the over-all electron driving force is directly related to the potential difference between the anode and cathode. In System 1 where a graphite carbon anode and cathode are used, it is very difficult to transfer electrons from the bacterial cell to the anode because of the lack of an electron channel or mediator that interacts with the cell membrane. Consequently, in System 1 current is low but the potential is high. In System 2, electrons transfer from the cell to the anode is difficult without an electron channel but transfer from the cathode to oxygen is enhanced by Fe$^{3+}$; thus, current produced is higher than in System 1 but the potential difference is the same. In Systems 3 and 4, electrons are easily transferred from the cell to the anode because neutral red or Mn$^{4+}$ serves as an electron channel; but the potential is lower than in Systems 1 or 2.

Previously, soluble electron mediators were used in fuel cells such as neutral red, thionin, and 2-hydroxyl-1,4-naphthoquinone to convert microbial reducing power into electricity. Most soluble electron donors except for neutral red cannot be easily bound to cells and all must be continually added or recycled. This problem can be solved by immobilizing the electron mediator (e.g. neutral red or Mn$^{4+}$) on the electrode.

In the present invention, the immobilization of neutral red to a carbon electrode has been improved by changing from a graphite plate electrode to a woven graphite electrode which has a surface area 1000 times greater. Also in the present invention, it has been demonstrated that a Mn$^{4+}$ graphite plate electrode works as well or better than a neutral red woven graphite in coupling electron transfer from microbes to electricity production in fuel cells. In sum, these two new anode compositions significantly enhanced electron transfer efficiencies in microbial fuel cells from that reported previously.

Resting cells in the new fuel cell system described here were using lactate as the electron donor and the anode as the electron acceptor for energy metabolism. The Mn$^{4+}$ graphite anode proved to be the best conductor of electron transfer from lactate dehydrogenation in cells to the Fe$^{3+}$ graphite cathode. Many different kinds of bacteria including *Escherichia Shewanella, Clostridium* and *Desulfovibaio* have been reported to reduce metallic ions (e.g. manganese, ferric, uranium and cupric) while oxidizing organic substrate (See, Lovley, D. R., "Dissimilatory Metal Reduction", *Annu. Rev. Microbiol.* 47:297-299, 1993).

A variety of microbes have been shown to be electrophilic. It has been reported that metabolizing methanogens can grow with electricity (i.e. the cathode) as the electron donor while reducing $CO_2$ as the electron acceptor (see, Park and Zeikus, "Electricity Generation In Microbial Fuel Cells Using Neutral Red And An Electronophore", *Appl. Environ. Microbiol.,* 66:1292-1297, 2000). Kim et al. in "Direct Electrode Reaction Of Fe(III)-Reducing Bacterium, *Shewanella Putrefacians*", *J. Microbial. Biotechnol.,* 9:127-13, 1999 demonstrated that *S. putrefacians*, which as iron containing cytochromes in its out membrane, can grow with lactate as the electron donor and a woven graphite anode as the electron acceptor.

Here, sewage sludge served as a better biocatalyst than *E. coli* for electricity generation (See Table A). Without intending to be bound by theory, it is presumed this is because the mixed anaerobic population can generate lower reducing power than *E. coli* because it contains microbes whose enzyme co-factors (e.g. $F_{420}$, ferredoxin, etc.) operate below −0.4 mv. It can be hypothesized that sewage sludge contains electrophiles (i.e. microbes especially adapted to use an electrode, as higher electron donors or acceptors for energy metabolism). These electrophilic species may have better electron transfer efficiencies than *E. coli*. In this regard, the prevalent coccoidal microbes in sewage sludge that dehydrogenated lactate on the neutral red woven graphite anode did not resemble either *E. coli* or *S. putrefacians*. Without intending to be bound by theory, it is believed that the $Mn^{4+}$ graphite and the neutral red-woven graphite electrodes and fuel cells described herein may prove useful as "lightning rods" for the enrichment of electrophiles.

Thus, the present invention provides a use of $Mn^{4+}$-graphite and neutral red-woven graphite electrodes to electrically recycle cofactors in oxidoreductase linked biocatalysis systems. The electrochemical bioreactor system using neutral red with resting cells can electrically recycle NADH, NADPH and ATP during cellular metabolism and biochemicals production. Furthermore, the electrochemical bioreactor system using neutral red or $Mn^{4+}$ with resting or growing cells can be used to produce electricity during microbial degradation. Also, the electrochemical bioreactor system using neutral red or $Mn^{4+}$ and oxidoreductases can be used to oxidize or reduce NAD during biochemicals production.

Example 6

Growth of Organisms

*Actinobacillus succinogenes* was grown in medium "A" containing 10 grams of glucose per liter, 5 grams of yeast extract per liter, 8.5 grams of sodium phosphate monobasic per liter, and 10 grams of sodium bicarbonate per liter under an anaerobic $N_2$—$CO_2$ (80:20) atmosphere at 37° C. in a 4 liter anaerobic bottle for 16 hours.

Example 7

Preparation of Fumarate Reductase

Cell extracts were prepared at 4° C. under an anaerobic $N_2$ atmosphere. The harvested and washed cells were resuspended in 100 mM Tris-HCl buffer (pH 7.2) containing 1 mM dithiothreitol (DTT) and 0.05 mg. of DNase. The bacterial cells were disrupted by passing them twice through a French press at 20,000 lb./in.$^2$. The cell debris was removed by centrifugation three times at 40,000×g for 30 minutes each time. The purified membranes were obtained from cell extracts by ultra-centrifugation at 100,000×g for 120 minutes. The clear brown precipitate was washed twice with 100 mM Tris-HCl buffer (pH 7.2) containing 1 mM DTT and resuspended in the same buffer containing 1 mM DTT by homogenization. The suspended membrane fraction was used as an enzyme source for the fumarate reductase.

Example 8

Electrode Composition and Preparation

A Fe(III)-graphite electrode was made from mixture of 60% (w/w) fine graphite powder (particle size below 600 mesh), 36% (w/w) kaolin as inorganic binder (particle size below 400 mesh), 3.0% (w/w) ferric ions and 1.0% (w/w) nickel ions. Distilled water was added to the mixture for making a graphite paste, and the paste was configured to a square-shaped plate (20 cm.×20 cm.×1 cm. thick) by pressing at 1.0 kg./cm.$^2$, drying on air for 48-72 hours at room temperature, and solidifying by baking at 1100° C. for 12 hours under anaerobic conditions using a kiln.

Example 9

Preparation of an Electrode Modified with CMC-NR-NAD$^+$-Fumarate Reductase Complex A graphite felt electrode modified with CMC-NR-NAD$^+$-fumarate reductase complex can be used as an anode or cathode for an electrode reaction according to the invention. A graphite felt electrode modified with carboxymethylcellulose, neutral red, NAD$^+$, and fumarate reductase was prepared as follows. First, a graphite felt electrode was formed as above in Example 8. The graphite felt electrode was then cleaned by soaking in methanol for 12 hours and then in deionized distilled water for 12 hours. The electrode was dried at 120° C. for 1 hour. The electrode was made in the carboxy form by heating at 200° C. for 2448 hours. The electrode was then soaked in dicyclohexylcarbodiimide solution (2 mg./ml., in chloroform) at 4° C. for 6 hours, and then dried in air. The electrode was soaked in neutral red (100 µM) solution in chloroform at 4° C. for 12 hours. The electrode was washed by soaking in methanol at 4° C. for 3 hours three times until the unbound neutral red was completely removed. The electrode was then dried at 40° C. for 5 hours.

The electrode was then soaked in a 0.07% carboxymethylcellulose (available from Sigma, C5678, low viscosity, average MW 700,000) solution in deionized distilled water. The electrode was dried at 60° C. for 6 hours until the electrode hardened. The electrode was then soaked in dicyclohexylcarbodiimide solution (2 mg./ml., in chloroform) at 4° C. for 6 hours, and then dried in air. The electrode was soaked in neutral red (100 µM) solution in chloroform at 4° C. for 12 hours. The electrode was washed by soaking in methanol at 4° C. for 3 hours three times until the unbound neutral red was completely removed. The electrode was then dried at 40° C. for 5 hours.

The electrode was then soaked in a 100 mM 1-cyclohexyl-3-(2-morpholinoethyl)carbodiimide metho-p-toluenesulfonate (CMCD) solution at 4° C. for 6-12 hours. The electrode was then soaked in 1 mM NAD$^+$ solution in Tris-HCl buffer (100 mM, pH 7.0) at 4° C. for 12 hours. The electrode was then washed in Tris-HCl buffer (100 mM, pH 7.0). The electrode was then soaked in a membrane fraction (protein concentration 1.635 mg./ml.) isolated from *Actinobacillus succinogenes* in Tris-HCl (100 mM, pH 7.0) at 4° C. for 12 hours. The treated electrode was dried at 4° C. in a refrigerator, and then tested for the oxidation-reduction reaction of succinate-fumarate.

It was believed that 0.35 mg. membrane protein was immobilized on 1 gram of graphite felt electrode, which is 0.07% of the total membrane protein. The concentration of NAD$^+$ bound to the graphite felt electrode can be determined from the concentration of membrane protein bound to graphite felt electrode. Because, 1 mM of NAD$^+$ was used for immobilization on the graphite felt electrode, the concentration of NAD$^+$ bound to electrode was believed to be below 0.0007 mM/G of graphite felt electrode. The fumarate reductase activity of the membrane protein is 9.5 µM NADH/mg. protein/min.

Example 10

Preparation of a Bioelectrochemical Reaction System

A one compartment electrochemical system suitable for use as a biosensor as shown in FIG. 9 was prepared as follows. An anode was prepared from 0.05 grams (diameter: 1.0 cm.; thickness: 0.6 cm.; surface area: 0.47 m$^2$/g) of the graphite felt electrode modified with carboxymethylcellulose, neutral red, NAD$^+$, and fumarate reductase as prepared in Examples 5-9. A cathode was prepared as a ferric ion (Fe$^{3+}$ or Fe(III))-graphite electrode having a surface area of 0.0000785 m$^2$ (0.785 cm$^2$). The inside diameter and the height of the reactor were 1 cm. and 0.6 cm., respectively. The thickness of the porcelain membrane and the anode were 0.1 mm. and 0.3 mm., respectively. The outside of the reactor was made from a rubber stopper. The bioelectrochemical oxidation of succinate to fumarate was coupled to electricity production, and the reduction of fumarate to succinate was used for biosynthesis. The cathode surface area used was adjusted to 0.3 g. (1.75×4.0×0.6 cm., 0.47 m²g) and the anode surface area was 0.0014 m². The volume of each of the anode and the cathode compartment was 15 milliliters. The two compartment system was made from glass, and the porcelain septum (thickness: 3 mm., 3×5 cm.) with micro-pores was used as an ion-selective membrane for separation of the anode from the cathode compartment.

Example 11

Electrochemical Reaction for Detection of Succinate

Zero, 1, 5, 50, 100, 200, 300 and 400 μM solutions of succinate in Tris-HCl buffer (100 mM, pH 7.0) were prepared for determining lower detectable concentration levels of succinate. With the system of FIG. 9, both amperes and potential were measured at the same time after a continuous flow of 10 ml. of succinate solution from the lowest concentration to the highest concentration under closed circuit condition and then without pausing of the current value, the succinate solution of the next concentration was applied. In addition, 1 to 10 mM of standard succinate solutions in Tris-HCl buffer (100 mM, pH 7.0) were prepared for determining the catalytic activity of the graphite felt electrode modified with CMC-NR-NAD$^+$-fumarate reductase complex. With the system of FIG. 9, the potential was measured after 5 minutes following the flow (flow rates, 5 ml./min.) of succinate solution on an open circuit system and the current was measured by changing from an open circuit to a closed circuit system. The highest value of current was chosen and then the current value was paused to zero value by maintaining of closed circuit system under stopped flow. After pausing, the succinate solution of the next concentration was applied to the system. The results are in FIGS. 12 and 13.

Example 12

Oxidation of Succinate to Fumarate Coupled to Electricity Production by Electrode Modified with CMC-NR-NAD$^+$-Fumarate Reductase About 6 mM of fumarate solution in Tris-HCl buffer, (100 mM, pH 7.0) was prepared for electricity consumption coupled to reduction of fumarate by the modified graphite felt electrode (cathode) with CMC-NR NAD$^+$-fumarate reductase that acts as a catalyst. Two control tests were done. In one control, the modified electrode with CMC-NR-NADH$^+$-fumarate reductase complex was used but no electricity was supplied, and in another control, 1 mM NADH was added to the reactor but no electricity was supplied. In the test reaction, the potential between the anode and the cathode was 2.0 volts and the current was variable from 8 to 10 milliamps but NADH was not added to the reactor. The anode and the cathode were separated by the porcelain septum (3 mm. thickness, 3×5) with micropores made from 100% kaolin by baking at 100° C. instead of a cation selective membrane (such as that sold under the trademark Nafion, Electrosynthesis). The results are in FIGS. 14 and 15.

Analytical Techniques for Examples 6-12

In the Examples 6-12, fumarate and succinate were quantitatively analyzed by an HPLC (Waters model) equipped with an Aminex Fast Acid column (100 mm.×7.8 mm, available from BioRad, Hercules, Calif., USA) and auto sampler.

Analysis for Examples 6-12

Figure 12:
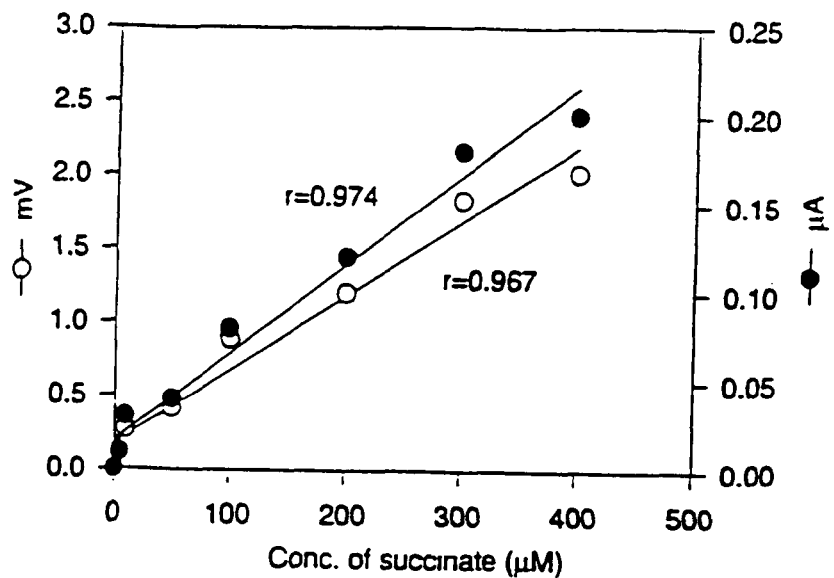
FIG. 12 is a graph showing succinate detection by a bioelectrochemical cell using a graphite felt electrode modified with CMC-NR-$NAD^+$-fumarate reductase complex according to the invention.

FIG. 12 shows the linear response rate between a lower concentration of succinate detected by the enzyme immobilized biosensor using the system of FIG. 9. The potential in millivolts and the current in milliamps were measured on closed circuit without external resistance. The lowest detection limit of succinate by the CMC-NR-NAD$^+$-fumarate reductase modified graphite electrode was 5 μM. The amount of membrane protein bound to the electrode was 0.35 mg./gram of graphite felt. The fumarate reductase activity of the membrane protein was 9.5 μM NADH/mg. protein/min.

Figure 13:
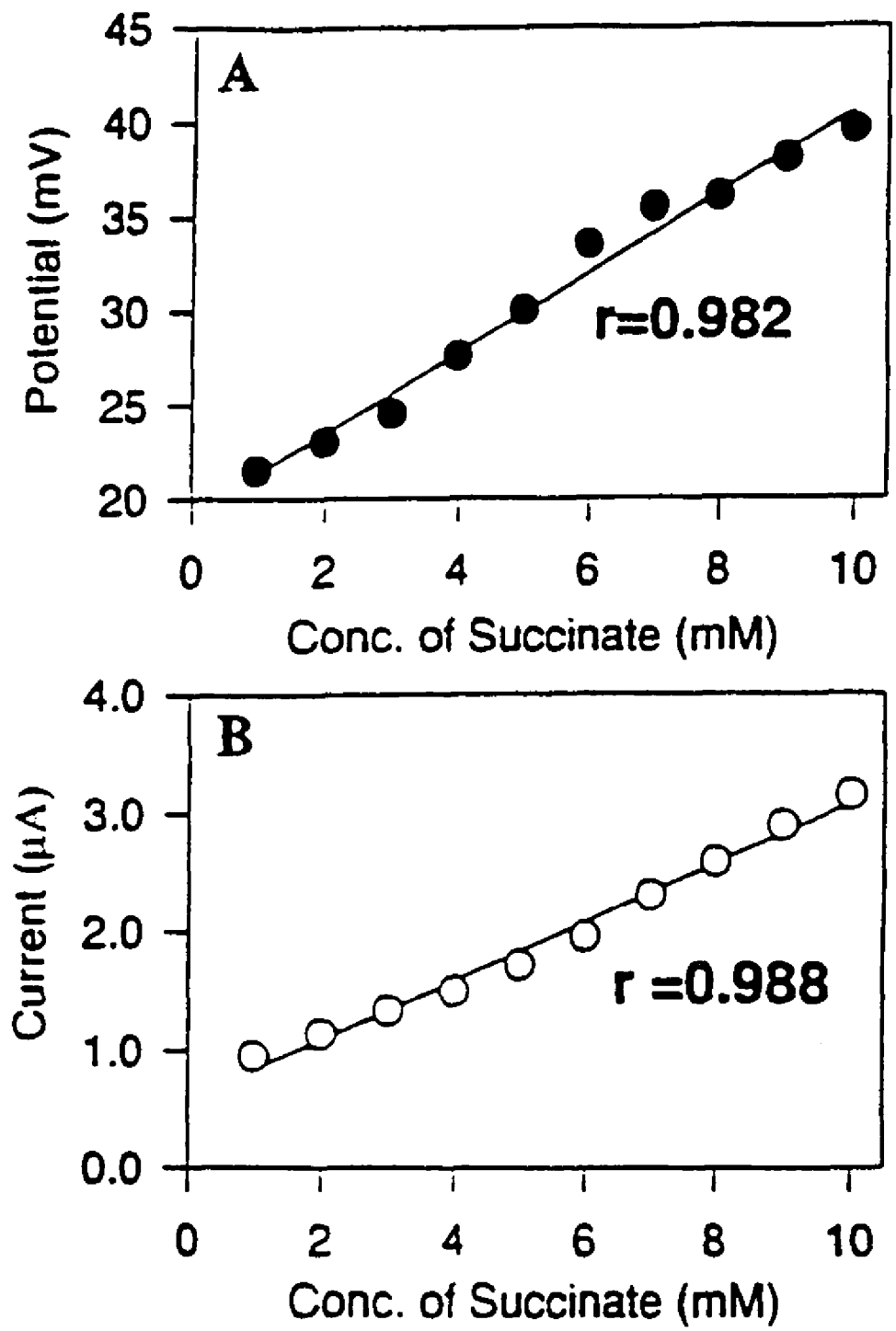
FIG. 13 is a graph showing the potentiometric and amperometric response of a bioelectrochemical cell using a graphite felt electrode modified with CMC-NR-$NAD^+$-fumarate reductase complex according to the invention.

FIG. 13 shows the relationship between higher succinate concentrations and current and potential generated by the immobilized enzyme chemical sensor. The potentiometric (graph A) and amperometric (graph B) response of the modified electrode with CMC-NR-NAD$^+$-fumarate reductase complex was measured at pH 7.0 and at 26° C. using the system of FIG. 9. Each point of the plot of FIG. 13 corresponds to the potential value after 5 minutes following the addition of succinate on an open circuit system. The current was measured on a closed circuit system. The amount of membrane protein bound to the electrode was 0.35 mg./gram of graphite felt. The fumarate reductase activity of the membrane protein was 9.5 μM NADH/mg. protein/min.

Figure 14:
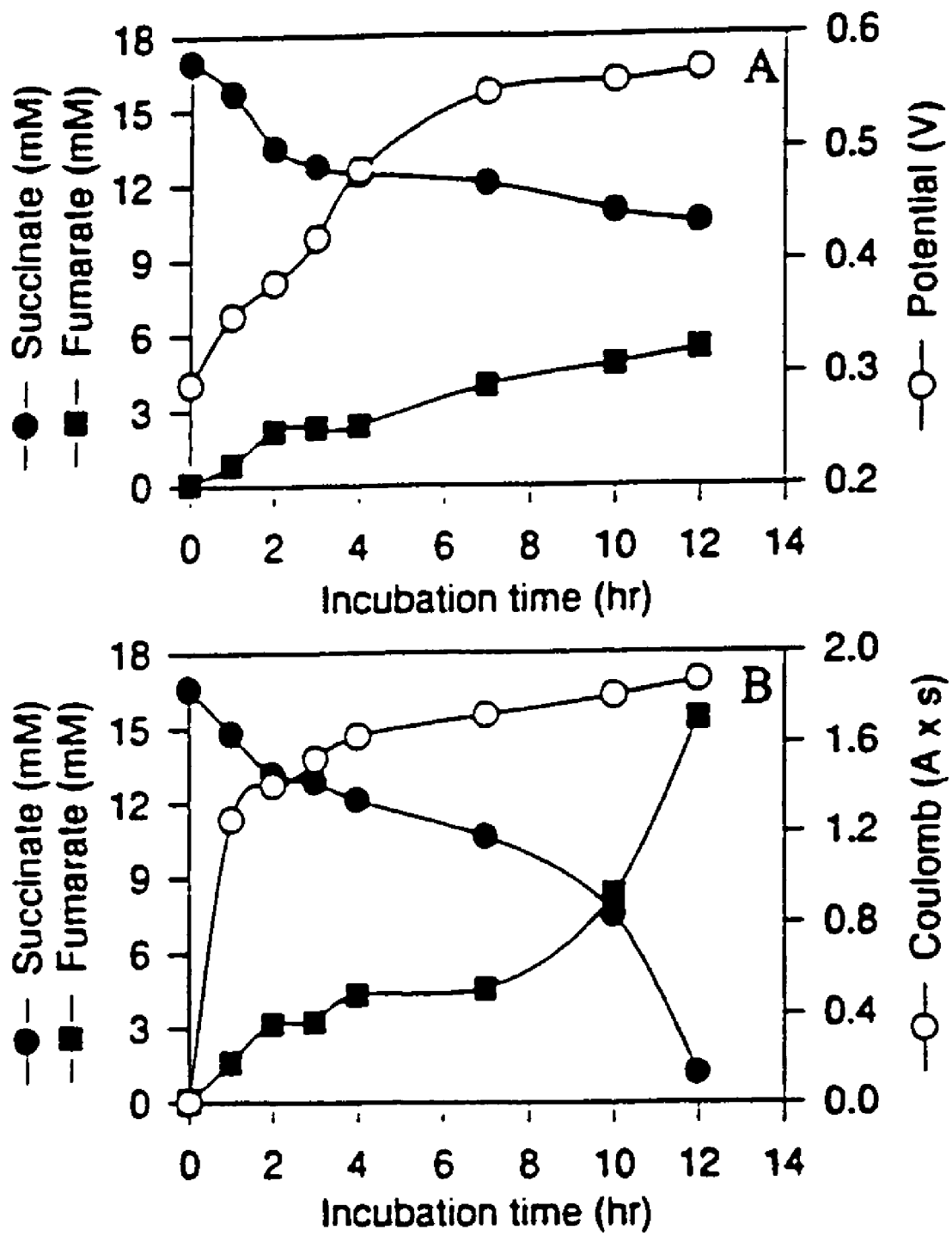
FIG. 14 is a graph showing the oxidation of succinate to fumarate on a graphite felt electrode modified with CMC-NR-$NAD^+$-fumarate reductase complex according to the invention.

FIG. 14 shows the relationship between electricity generation and the amount of fumarate produced during succinate oxidation by the immobilized enzyme electrode. The oxidation of succinate to fumarate on the graphite felt electrode modified with CMC-NR-NAD$^+$-fumarate reductase complex, which was coupled to electricity production in an open circuited (graph A) and closed circuited (graph B) biofuel cell system, was measured. The anode was the graphite felt electrode modified with CMC-NR-NAD$^+$-fumarate reductase complex and the cathode was Fe(III)-graphite. The anode surface area was adjusted 0.3 g. (0.47 m²/g) and the cathode surface area was 0.0014 m² (14 cm.²). The amount of membrane protein bound to the electrode was 0.35 mg./gram of graphite felt. The fumarate reductase activity of the membrane protein was 9.5 μM NADH/mg. protein/min. Electricity and fumarate production correlated with the amount of succinate consumed.

Figure 15:
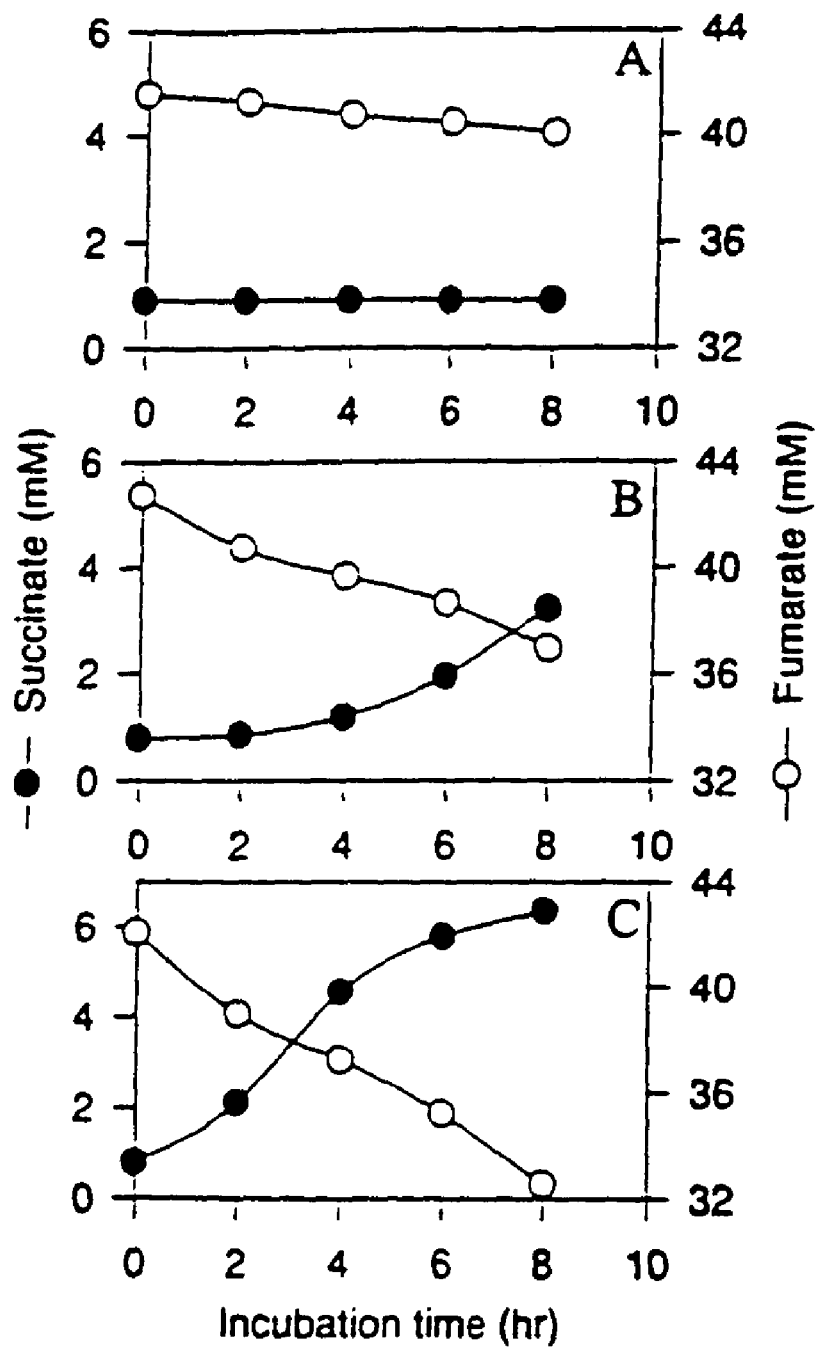
FIG. 15 is a graph showing the reduction of fumarate to succinate on a graphite felt electrode modified with CMC-NR-$NAD^+$-fumarate reductase complex according to the invention.

The reduction of fumarate to succinate on the graphite felt electrode modified with CMC-NR-NAD$^+$-fumarate reductase complex as a catalyst was measured. In graph A of FIG. 15, electricity was not supplied and NADH was not added to the reactor. In graph B of FIG. 15, electricity was not supplied and 1 mM of NADH was added to the reactor. In graph C of FIG. 15, 2 volts of direct current electrical power were supplied at 8-10 milliamps. The cathode was the graphite felt electrode modified with CMC-NR-NAD$^+$-fumarate reductase complex and the anode was Fe(III)-graphite. The cathode surface area was adjusted 0.3 g. (0.47 m²/g) and the anode surface area was 0.0014 m² (14 cm.²). The amount of membrane protein bound to the electrode was 0.35 mg./gram of graphite felt. The fumarate reductase activity of the membrane protein was 9.5 μM NADH/mg. protein/min. FIG. 15 shows that in the absence of electricity, the reduction of fumarate to succinate by the immobilized enzyme electrode was insignificant (graph A), whereas, considerable more succinate was produced from electricity (graph C) than from NADH (graph B). This occurred because the electrical reduction of neutral red chemically reduces NAD and both electron carriers are utilized by the fumarate reductase.

Example 13

Growth of Organisms

*Actinobacillus succinogenes* was grown in a medium A (10 g of glucose per liter, 5 g of yeast extract per liter, 8.5 g of sodium phosphate monobasic per liter, 10 g of sodium bicarbonate per liter) under an anaerobic $N_2$—$CO_2$ (80:20) atmosphere at 37° C. in 4 liter anaerobic bottle for 16 hours. Resting cells of *Actinobacillus succinogenes* were prepared by harvesting stationary-phase cultures at 4° C. by centrifugation at 5,000×g. The cells were washed twice in resuspended medium (50 mM phosphate buffer, pH 7.0) under anaerobic condition. Bacterial density was determined by spectrophotometer at 660 nm as an optical density (OD). In all experiments bacterial cells were used right after harvesting without storage in a refrigerator.

Example 14

Preparation of a Bioelectrochemical System

A two compartment (anolyte and catholyte) electrochemical cell was used as a control for comparison of the effects of anode-cathode combinations on succinate production by bioelectrochemical reduction of fumarate. The two compartment electrochemical system was separated by a porcelain septum made from 100% Kaolin, diameter 50 mm and thickness 3 mm into an anode and cathode compartment. Fe (III)-graphite (0.0088 $m^2$) was used in an anode in all experiments, but either a Mn(IV)-graphite (0.008 $m^2$), normal graphite felt (2.8 g, 0.47 $m^2$g) or modified graphite felt (2.8 g, 0.47 $m^2$/g) with bound NR was used as a cathode for comparison of the effect on electrochemical reduction of fumarate, respectively. During the experiments, completely anoxic conditions were maintained in the cathode compartment by gassing with $N_2$—$CO_2$ (80:20) gas mixture. The flow rate was adjusted to 300 ml/min. The trace oxygen contained in the mixture gas was removed in a furnace filled with pure copper fillings at 370° C. No gassing and no agitation were used in the anode compartment.

Example 15

Preparation of Electrodes

The Fe (III)-graphite anode was made from a mixture of 60% (w/w) fine graphite powder (particle size was below 600 mesh), 36% (w/w) inorganic binder (mainly Kaolin of which particle size was below 400 mesh), 3.0% (w/w) ferric ion and 1.0% (w/w) nickel ion. The Mn(IV)-graphite cathode was made from a mixture of 60% (w/w) fine graphite powder, 37% (w/w) inorganic binder (Kaolin, white clay), 2.0% (w/w) manganese ion and 1.0% (w/w) nickel ion, respectively. Distilled water was added to the mixture for making a paste, and the paste was configured into a square-shaped plate (20 cm×20 cm×1 cm thickness) by pressing at 1.0 kg/$cm_2$, drying on air for 24 hours-48 hours at room temperature and solidified by baking at 1100° C. for 12 hour under anaerobic conditions using a Kiln.

Example 16

Immobilization of Neutral Red to Graphite Woven Electrode

Neutral red was immobilized to the felt electrode by following procedure: (1) Cleaning a graphite felt electrode by soaking in methanol for 12 hours and then in deionized distilled water for 12 hours. (2) Drying the electrode at 120° C. for 1 hour. (3) Making the carboxy form by heating at 200° C. for 24 hours-48 hours. (4) Soaking the electrode in dicyclohexycarbodiimide solution (2 mg/ml, in chloroform) at 4° C. for 6 hours. (5) Drying the electrode in air. (6) Soaking the electrode in neutral red (100 µM) solution in chloroform at 4° C. for 12 hours. (7) Washing the electrode by soaking in methanol at 4° C. for 3 hours three times until the unbound neutral red is completely removed. (8) Drying electrode at 40° C. for 5 hours.

Example 17

Electrochemical Reduction of Fumarate to Succinate by Growing Cells of *Actinobacillus succinogenes*

A 300 ml sample of fresh medium A with 60 mM fumarate was used as a catholyte and 300 ml of 200 mM $KH_2PO4$ was used as an anolyte. After autoclave, the dissolved oxygen in the catholyte was removed by gassing with a $N_2$—$CO_2$ (80:20) mixture at flow rates of 1 liter/min. for 30 min and then the flow rate was adjusted to 300 ml/min. 30 ml of precultivated bacterial cells were inoculated into the catholyte and 2 volt electricity was supplied during experiments. Mn(IV)-graphite electrode, modified graphite felt with NR and normal graphite felt electrode were compared to each other. The reactor without an electrode and NR was used as a control. The soluble (100 µM) was added to the reactor with a normal graphite felt electrode. Two volts of electricity were used as reducing power. The culture sample was aseptically isolated from reactor and used for analysis after centrifugation at 13000×g for 30 min and then by filtration with a membrane filter (pore size, 0.22 µM). Fumarate and succinate were quantitatively analyzed by HPLC (Waters model) equipped with Aminex Fast Acid column (100 mm×7.8 mm, BioRad, 2000 Alfred Nobel drive, Hercules, Calif. (94547)) and an auto sampler.

Example 18

Electrochemical Reduction of Fumarate to Succinate by Resting Cells of *Actinobacillus succinogenes*

The harvested bacterial cells after 16 hours of cultivation were used as a biocatalyst. 300 ml of fresh medium A with 60 MM fumarate was used as a catholyte and 300 ml of 200 mM $KH_2PO4$ was used as an anolyte. After autoclaving the dissolved oxygen in catholyte was removed by gassing with $N_2$—$CO_2$ (80:20) mixture at flow rates of 1 liter/min. for 30 min and then the flow rate was adjusted to 300 ml/min. 30 ml of pre-cultivated bacterial cells were inoculated into the catholyte and 2 volt electricity was supplied during the experiments. The Mn(IV)-graphite electrode, the modified graphite felt with NR electrode and the normal graphite felt electrode were compared to each other. The reactor without an electrode and NR was used as a control. The soluble NR (100 µM) was added to the reactor with a normal graphite electrode. 2 volt electricity was used as a source of reducing power. The culture samples were aseptically isolated from the reactor and were used for analysis after centrifugation at 13000×g for 30 min and then filtered with a membrane filter (pore size, 0.22 µM). Fumarate and succinate were quantitatively analyzed by HPLC (Waters model) equipped with Aminex Fast Acid column (100 mm×7.8 mm, BioRad, 2000 Alfred Nobel drive, Hercules, Calif. (94547)) and an auto sampler.

Example 19

Electrochemical Reduction of $NAD^+$ on Mn(IV)-Graphite Cathode 1 mM $NAD^+$ was tested for electrochemical reduction coupled to oxidation-reduction reaction of a Mn(IV)-graphite electrode in a 30 ml electrochemical reactor, 0.0014 $m^2$. if Mn(IV)-graphite and Fe(III)-graphite were used as a cathode and anode, respectively. 0.141 $m^2$. of graphite felt cathode and 0.0014 $m^2$ of $Fe^{+3}$-graphite anode were used for comparison. Two volts of electricity were applied and the current was varied from 5 to 10 mA.

Analysis for Examples 13-19

Figure 16:
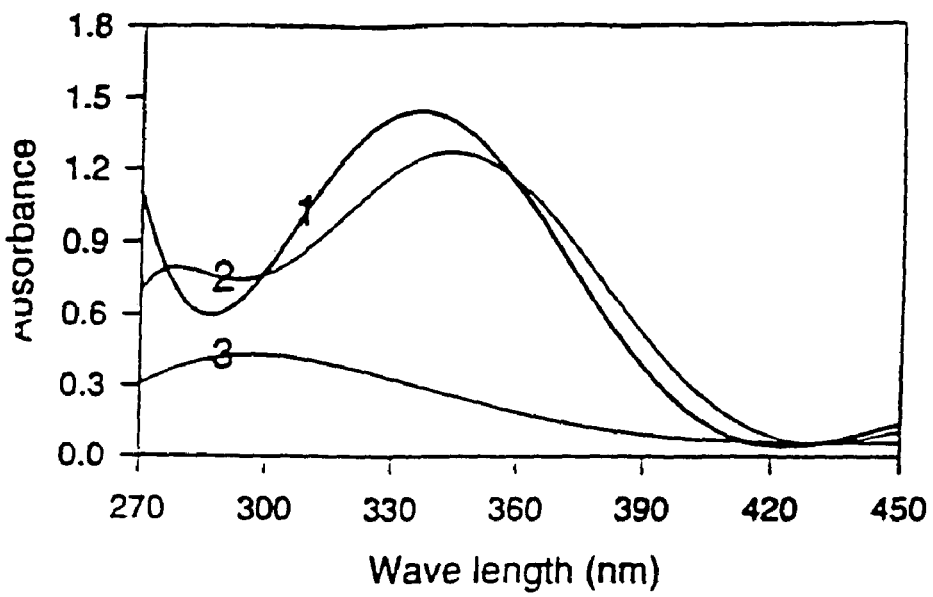
FIG. 16 shows that a $Mn^{+4}$ graphite electrode according to the invention can electrochemically reduce $NAD^+$ to NADH.
Figure 17:
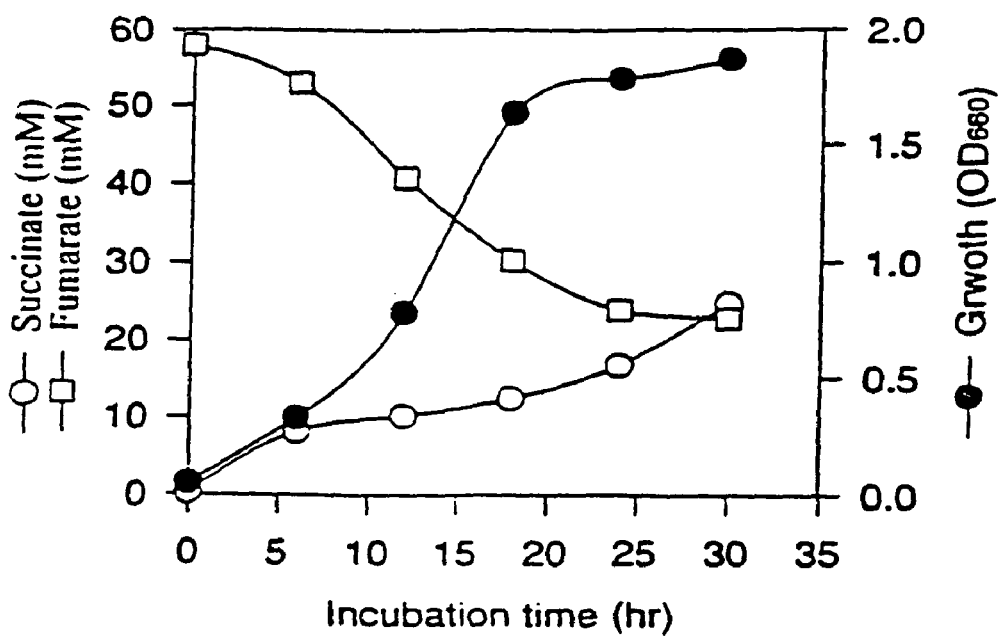
FIG. 17 shows a controlled fumarate fermentation by *A. succinogenes* without electricity, that is a reduction of fumarate to succinate by growing cells of *Actinobacillus succinogenes* in a bioreactor without electrochemical reaction.
Figure 18:
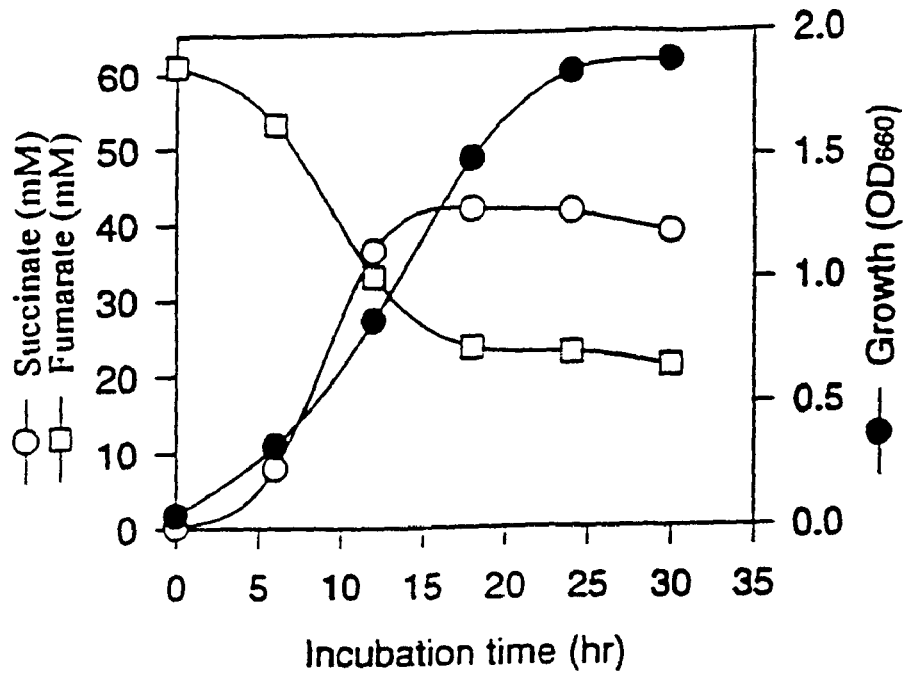
FIG. 18 shows the reduction of fumarate to succinate by growing cells of *Actinobacillus succinogenes* in an electrochemical reactor using a Mn(IV)-graphite electrode as the cathode. A Fe(III)-graphite electrode was used as the anode. The density of the binding cell to anode was 0.12 as $OD_{660}$. The binding bacterial cells to electrode were calculated using a predetermined calibration curve (bacterial density ($OD_{660}$)=bacterial protein concentration (mg/ml)×1.7556). Protein of the binding bacterial cell to electrode was obtained by the alkaline lysis method (see, Park et al., "Utilization Of Electrically Reduced Neutral Red By *Actinobacillus Succinogenes*: Hysiological Function Of Neutral Red In Membrane-Driven Fumarate Reduction And Energy Conservation", *J. Bacteriol.* 1812:2403-2410, 1999).

In order for an electron mediator to be effective in electron transfer from a cathode into microbial metabolism, it needs to be able to reduce NAD and not be toxic to cells. FIG. 16 shows that the $Mn^{+4}$ graphite electrode can electrochemically reduce $NAD^+$ to NADH. The electron transfer efficiency of the $Mn^{+4}$ graphite electrode was then compared to other cathode compositions (Table 1) during fermentation of fumarate to succinate by *A. succinogenes* in a two chamber electrochemical bioreactor system. Clearly, the $Mn^{+4}$ graphite cathode allowed more electricity to be utilized and more succinate to be produced than with either the neutral red-bound graphite electrode, soluble neutral red and a graphite electrode, or the graphite electrode alone. When an electron mediator was used, somewhat less cells were produced. The $Mn^{+4}$ graphite electrode was clearly better at electron transfer into cells than the other electrodes compositions tested. Therefore, the effect of several physiological parameters on electricity utilization and succinate production by *A. succinogenes* using the $Mn^{+4}$ graphite cathode and $Fe^{+3}$ anode were examined. FIG. 17 shows a control fumarate fermentation by *A. succinogenes* without electricity and, FIG. 18 shows the same conditions but with electricity. It is clear that electricity significantly increases succinate production without altering fumarate consumption or growth.

Figure 19:
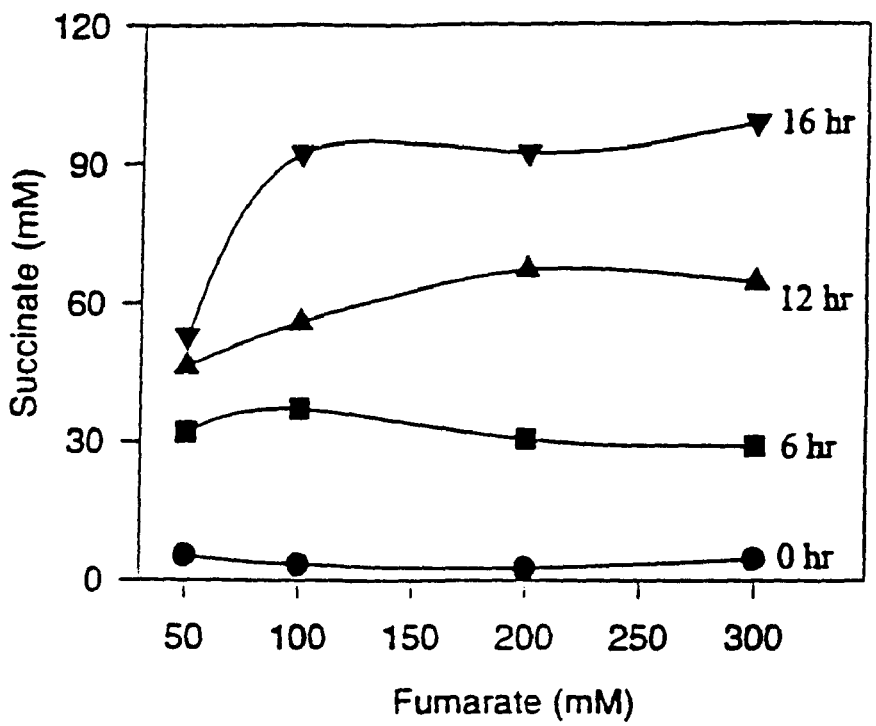
FIG. 19 shows the effect of substrate concentration on the bioelectrochemical reduction of fumarate to succinate. Resting cells of *Actinobacillus succinogenes* were used. The cell density was adjusted to 4.0 ($OD_{660}$). The Fe(III)-graphite and Mn(IV)-graphite were used as anode (160 $cm^2$ surface area) and a cathode (160 $cm^2$ surface area) respectively.

FIG. 19 shows that the resting cells suspensions (i.e. stationary growth phase of O.D. 4.0) can convert fumarate into succinate at significant rates. Resting cells appeared to electrically reduce fumarate into succinate at an optimal 0.9 ratio at 100 mM fumarate and 16 hours (see FIG. 19) Table 2 compares the influence of different physiological parameters on succinate production from fumarate in the absence or presence of electricity. In the absence of electricity, growing cells produce lower levels of succinate than with electricity. Resting cells without electricity produce more succinate than growing cells with electricity and have significantly higher levels of electricity utilization.

TABLE 1

Effect Of Electron Mediation System Conditions On Electrical Utilization, Growth And Succinate Production - (Fe(III)-Graphite Was Used As Anode In All Systems)

| Conditions | Electricity Utilized (mA) | Final Biomass $OD_{660}$ | Succinate Productivity | |
|---|---|---|---|---|
| | | | Concentration (mM) | Mol succinate/ mol fumarate |
| No mediator/ graphite | 1.3-1.8 | 2.46 | 24.71 | 0.556 |
| Soluble NR/ Graphite | 4.0-4.6 | 1.91 | 21.90 | 0.718 |
| Neutral Red - Graphite | 3.3-3.6 | 1.85 | 32.71 | 0.758 |
| Mn - Graphite | 6.3-8.7 | 1.99 | 38.60 | 0.894 |

TABLE 2

Comparison Of Physiological Growth Parameters On Succinate Production And Productivity In The Absence Versus The Presence Of Electricity.

| Conditions | Electricity Utilized (mA) | Final Biomass $OD_{660}$ | Succinate Production (mM) | Succinate Productivity (mM biomass$^{-1}$, initial fumarate conc.$^{-1}$)[a] |
|---|---|---|---|---|
| Growing cells without electricity | 0 | 2.46 | 24.7 | 0.1673 |
| Growing cells with electricity | 6.3-8.7 | 1.99 | 38.6 | 0.3232 |
| Resting cells without electricity[b] | 0 | 3.0 | 11.5 | 0.0638 |
| Resting cells with electricity | 8.3-10.6 | 2.0 | 42.0 | 0.3500 |
| Resting cells with electricity | 9.5-12.2 | 4.0 | 52.9 | 0.2204 |

[a]initial fumarate concentration used was 60 mM
[b]which were extracted as in Park and Zeikus, "Electricity Generation In Microbial Fuel Cells Using Neutral Red And An Electronophore", Appl. Environ. Microbiol. 66: 1292-1297, 2000.
Resting cells were obtained from 16 hour cultivated culture by aseptic centrifugation.
Anode and cathode used were Fe(III)-graphite and Mn(IV)-graphite, respectively.

Therefore, it can be seen that the invention provides an electrochemical bioreactor system having improved electrodes that enhance the rate of electron transfer from cells. The electrochemical bioreactor system has an improved electrode that has utility as an enzymatic fuel cell, as a sensor for succinate detection, and as an engineered catalyst for the synthesis of fumarate or succinate. The electrochemical bioreactor system can be used as either an enrichment device for electrophilic microorganisms; that is, those which use an electrode as an electron acceptor, or electron donor for energy conservation.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

INDUSTRIAL APPLICABILITY

The invention relates to improved electrodes for electrochemical bioreactor systems that can use electrical energy as a source of reducing power in fermentation or enzymatic reactions and that can use electron mediators and a biocatalyst, such as cells or enzymes, to produce electricity.

What is claimed is:

1. An electrochemical bioreactor system comprising:
a first compartment containing a first electrode;
a second electrode;
an electrically conductive material connecting the first electrode and the second electrode;
an electrolyte for providing ionic conductivity between the first electrode and the second electrode; and
a biocatalyst disposed in the first compartment or associated with the first electrode,
wherein the first electrode comprises a metal ion electron mediator.

2. The electrochemical bioreactor system of claim 1 wherein:
the biocatalyst comprises cells of *Actinobacillus succinogenes* and the cells are disposed in the first compartment.

3. The electrochemical bioreactor system of claim 1 wherein:
the biocatalyst comprises cells of *Escherichia coli* and the cells are disposed in the first compartment 4. The electrochemical bioreactor system of claim 1 wherein:
the biocatalyst comprises sewage sludge and the sewage sludge is disposed in the first compartment.

5. The electrochemical bioreactor system of claim 1 wherein:
the second electrode includes a first surface and a second opposed surface, the electrolyte is disposed on the first surface, the first surface faces an interior of the first compartment, and the second surface comprises an exterior surface of the first compartment.

6. The electrochemical bioreactor system of claim 1 wherein:
the metal ion electron mediator is an iron cation.

7. The electrochemical bioreactor system of claim 1 wherein:
the metal ion electron mediator is $Fe^{3+}$.

8. The electrochemical bioreactor system of claim 7 further comprising:
an electrical power supply electrically connected to the electrically conductive material,
wherein electrical current is applied from the electrical power supply to the first electrode and the second electrode such that the first electrode acts as a cathode whereby the electrochemical bioreactor system promotes chemical synthesis in the first compartment.

9. The electrochemical bioreactor system of claim 8 wherein:
the biocatalyst comprises cells of *Actinobacillus succinogenes* and the cells are disposed in the first compartment,
wherein the electrochemical bioreactor system promotes the reduction of fumarate to succinate in the first compartment.

10. The electrochemical bioreactor system of claim 7 further comprising:
an electrical load electrically connected to the electrically conductive material,
wherein the first electrode acts as a anode and the electrochemical bioreactor system generates electrical current detectable at the load.

11. The electrochemical bioreactor system of claim 10 wherein:
the biocatalyst comprises cells of *Actinobacillus succinogenes* and the cells are disposed in the first compartment.

12. The electrochemical bioreactor system of claim 10 wherein:
the biocatalyst comprises cells of *Escherichia coli* and the cells are disposed in the first compartment.

13. The electrochemical bioreactor system of claim 10 wherein:
the biocatalyst comprises sewage sludge and the sewage sludge is disposed in the first compartment.

14. The electrochemical bioreactor system of claim 1 wherein:
the metal ion electron mediator is a manganese cation.

15. The electrochemical bioreactor system of claim 1 wherein:
the metal ion electron mediator is $Mn^{4+}$.

16. The electrochemical bioreactor system of claim 15 further comprising:
an electrical power supply electrically connected to the electrically conductive material,
wherein electrical current is applied from the electrical power supply to the first electrode and the second electrode such that the first electrode acts as a cathode whereby the electrochemical bioreactor system promotes chemical synthesis in the first compartment.

17. The electrochemical bioreactor system of claim 16 wherein:
the biocatalyst comprises cells of *Actinobacillus succinogenes* and the cells are disposed in the first compartment,
wherein the electrochemical bioreactor system promotes the reduction of fumarate to succinate in the first compartment.

18. The electrochemical bioreactor system of claim 15 further comprising:
an electrical load electrically connected to the electrically conductive material,
wherein the first electrode acts as a anode and the electrochemical bioreactor system generates electrical current detectable at the load.

19. The electrochemical bioreactor system of claim 18 wherein:
the biocatalyst comprises cells of *Actinobacillus succinogenes* and the cells are disposed in the first compartment.

20. The electrochemical bioreactor system of claim 18 wherein:
the biocatalyst comprises cells of *Escherichia coli* and the cells are disposed in the first compartment.

21. The electrochemical bioreactor system of claim 18 wherein:
the biocatalyst comprises sewage sludge and the sewage sludge is disposed in the first compartment.

* * * * *

UNITED STATES PATENT AND TRADEMARK OFFICE
CERTIFICATE OF CORRECTION

| | |
|---|---|
| PATENT NO. | : 7,838,282 B2 |
| APPLICATION NO. | : 11/881846 |
| DATED | : November 23, 2010 |
| INVENTOR(S) | : Joseph Gregory Zeikus and Doo Hyun Park |

It is certified that error appears in the above-identified patent and that said Letters Patent is hereby corrected as shown below:

Column 5, line 30, "(e.g., $Fe^3+$)" should be -- (e.g., $Fe^{3+}$) --.

Column 5, line 63, "and % aeration" should be -- and aeration --.

Column 9, line 55, "(e.g., $Fe^3+$)" should be -- (e.g., $Fe^{3+}$) --.

Column 18, line 9, "for 2448 hours" should be -- for 24-48 hours --.

Claim 3, Column 25, line 23, "compartment" should be -- compartment. --.

Signed and Sealed this
Twenty-second Day of March, 2011

David J. Kappos
*Director of the United States Patent and Trademark Office*